United States Patent
Akassoglou et al.

(10) Patent No.: US 12,016,934 B2
(45) Date of Patent: Jun. 25, 2024

(54) ANIMAL MODEL FOR SARS-CoV-2-SPIKE INDUCED COAGULOPATHY

(71) Applicant: The J. David Gladstone Institutes, a testamentary trust established under the Will of J. David Gladstone, San Francisco, CA (US)

(72) Inventors: Katerina Akassoglou, San Francisco, CA (US); Warner Greene, San Francisco, CA (US); Jae Kyu Ryu, San Francisco, CA (US); Mauricio Montano, San Francisco, CA (US)

(73) Assignee: The J. David Gladstone Institutes, a testamentary trust established under the Will of J. David Gladstone, San Francisco, CA (US)

( * ) Notice: Subject to any disclaimer, the term of this patent is extended or adjusted under 35 U.S.C. 154(b) by 0 days.

(21) Appl. No.: 17/552,464

(22) Filed: Dec. 16, 2021

(65) Prior Publication Data

US 2022/0184233 A1    Jun. 16, 2022

Related U.S. Application Data

(60) Provisional application No. 63/126,044, filed on Dec. 16, 2020.

(51) Int. Cl.
*A61K 49/00* (2006.01)
*A01K 67/00* (2006.01)
*G01N 33/50* (2006.01)

(52) U.S. Cl.
CPC .......... *A61K 49/0008* (2013.01); *A01K 67/00* (2013.01); *G01N 33/5088* (2013.01); *A01K 2227/105* (2013.01); *A01K 2267/0337* (2013.01); *G01N 2333/165* (2013.01)

(58) Field of Classification Search
CPC ................ A61K 49/0008; A01K 67/00; A01K 2227/105; A01K 2267/0337; G01N 33/5088; G01N 2333/165
See application file for complete search history.

(56) References Cited

PUBLICATIONS

Kobinger et al, Human Immunodeficiency Viral Vector Pseudotyped with the Spike Envelope of Severe Acute Respiratory Syndrome Coronavirus Transduces Human Airway Epithelial Cells and Dendritic Cells, (Human Gene Therapy 18:413-422 (May 2007)) (Year: 2007).*
Letko et al, Functional assessment of cell entry and receptor usage for SARS-CoV-2 and other lineage B betacoronaviruses, (Nature Microbio., vol. 5, Mar. 2020 (Year: 2020).*
Boudewijns et al STAT2 signaling restricts viral dissemination but drives severe pneumonia in SARS-CoV-2 infected hamsters, Nature Com., 11:5838, 2020 (Year: 2020).*
Schmidt et al, Measuring SARS-CoV-2 neutralizing antibody activity using pseudotyped and chimeric virusesJ Exp Med (2020) 217(11): e20201181. (Year: 2020).*

* cited by examiner

*Primary Examiner* — Emily A Cordas
*Assistant Examiner* — Constantina E Stavrou
(74) *Attorney, Agent, or Firm* — Schwegman Lundberg & Woessner, P.A.

(57) ABSTRACT

Described herein is an animal model useful for identifying therapeutic agents that can inhibit the physiological effects or symptoms of COVID-19 infection, including the effects of the following on one or more organs of the animal: inflammation, oxidative stress, fibrin deposition, blood brain barrier breakdown, clotting, and vascular problems.

14 Claims, 8 Drawing Sheets

Specification includes a Sequence Listing.

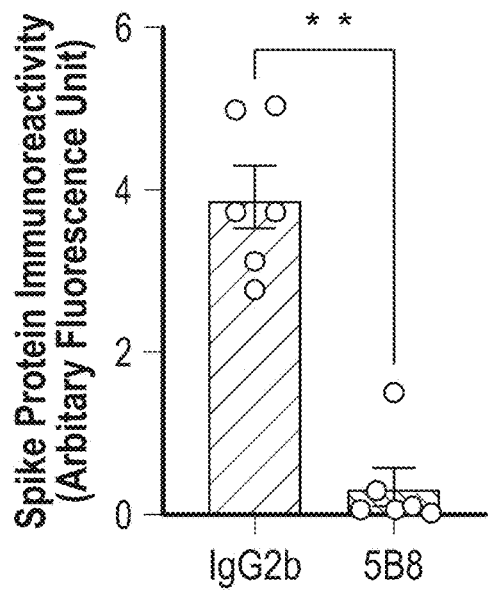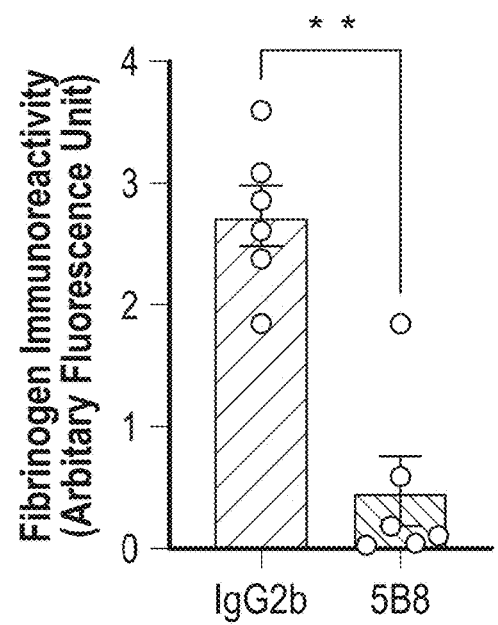
FIG. 7B
FIG. 7C
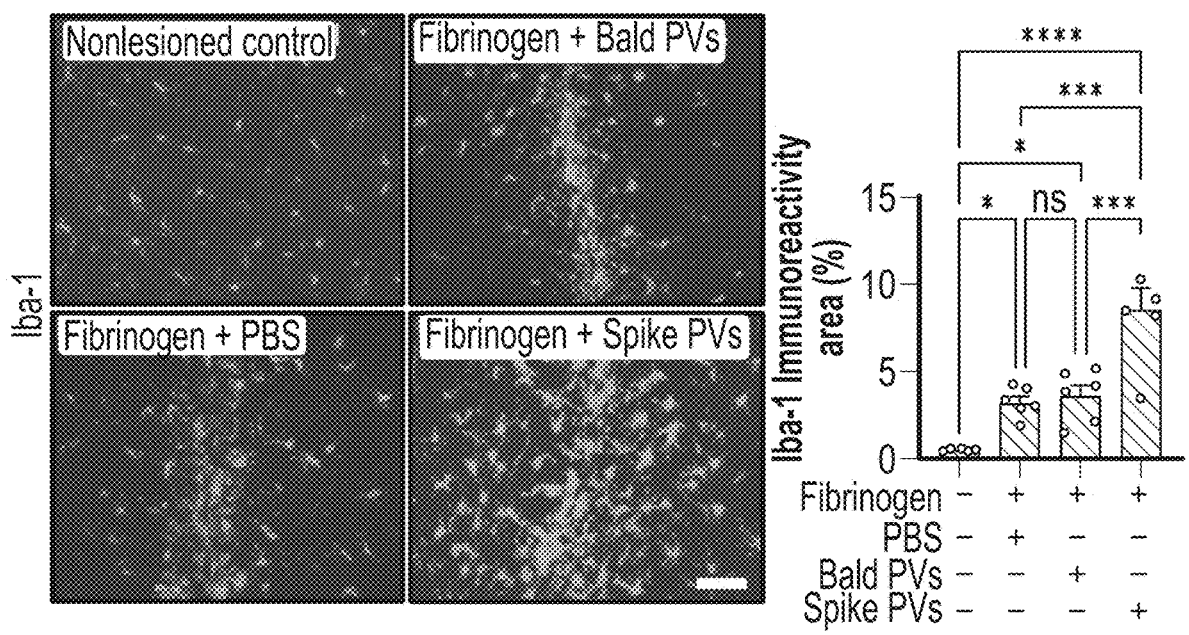
FIG. 8

ANIMAL MODEL FOR SARS-CoV-2-SPIKE INDUCED COAGULOPATHY

CROSS REFERENCE TO RELATED APPLICATIONS

This application claims the benefit of priority to U.S. Provisional Patent Application Ser. No. 63/126,044 entitled "Animal Model for SARS-CoV-2-Spike Induced Coagulopathy," filed Dec. 16, 2020, the complete disclosure of which is incorporated herein by reference in its entirety.

BACKGROUND

SARS-CoV-2 is highly infectious coronavirus that caused a global pandemic beginning in 2019 (COVID-19). Highly effective and safe RNA and adenoviral vaccines have been developed, but vaccine hesitancy, lack of vaccine access in the developing world, and the repeated emergence of viral variants displaying increased infectivity and/or immuno-evasive properties has left hundreds of millions of people around the globe vulnerable to the debilitating and lethal effects of this virus. Thrombosis and inflammation are hallmarks of acute coronavirus infection. Effective anti-thrombotic therapy has been difficult to achieve in part due to diminished clot breakdown. Glucocorticoids are partially effective in blunting the host inflammatory response that ultimately drives the lethal effects of viral infection. Even when infected individuals ward off the initial viral illness, they remain vulnerable to Long COVID or Post-Acute Sequelae of COVID-19 (PASC) that can involve multiple organs including the lung, heart, brain, and joints. No effective therapies have been identified for Long COVID although multiple reports suggest that Spike-based vaccinations are beneficial. Without question, more effective therapeutic approaches to manage both acute COVID-19 and Long COVID are urgently needed.

SUMMARY

Described herein are animal models useful for screening test agents that can be used for treatment of the physiological effects or symptoms of SARS-CoV-2 infection. Also described herein are methods for making the animal models and using the animal model for identifying useful therapeutic agents. The animal model is an animal to which pseudotyped virions expressing the SARS-CoV-2 Spike protein are administered. For example, to model acute SARS-CoV-2 infection, pseudotyped virions in amounts ranging between about 1 ng to 10,000 ng HIV p24Gag can be injected.

Persistent Spike expression may play a central role in Long COVID. Hence, the pseudotyped virions expressing the SARS-CoV-2 Spike protein can be infused or administered over time to the animals as a model of Long Covid. For example, pseudotyped virions in amounts ranging between 0.01-1 ng HIV p24Gag can be injected weekly to provide an animal model of Long Covid. This is about 100-fold to 10,000-fold less than is used for an animal model of acute SARS-CoV-2.

Pseudotyped viruses (PVs) are replication-defective viral particles formed with a structural and/or enzymatic core from one virus and an envelope glycoprotein of another. For example, the virions can be HIV Env-deficient virions pseudotyped with the SARS-CoV-2 Spike protein so that the SARS-CoV-2 Spike protein is displayed on the surface of the HIV Env-deficient viral particles. The SARS-CoV-2 Spike protein present on these virions directs their binding to angiotensin II converting enzyme (ACE2) receptors on the surface of target cells and subsequent entry into cells. As illustrated herein, the symptoms exhibited by this model animal include inflammation and oxidative stress in organs such as the lungs, heart and brain; disruption of the blood brain barrier; increased clot formation; and deposition of fibrin in the lungs, brain and heart. Test agents can be administered to the model animal that received the pseudotyped virions expressing the SARS-CoV-2 Spike protein to observe and/or quantify the effects of the test agent on these symptoms.

The effects of the test agent(s) on the symptoms of the SARS-CoV-2 can be observed, measured, and/or quantified and compared to a control. The control animal can be an animal of the same species and/or genotype who did not receive the SARS-CoV-2 Spike pseudotyped virions, or a control animal who received 'BALD' virions that do not express or display Spike proteins, or a combination of such control animals can be used.

DESCRIPTION OF THE FIGURES

FIG. 1A is schematic diagram illustrating the components used to make the SARS-COV-2 Spike pseudotyped virions and how to produce the SARS-CoV-2 Spike pseudotyped virions. As shown, an HIV Env-deficient packaging vector and an expression vector for SARS-CoV-2 Spike protein are transfected, for example, into HEK 293T cells, the cells are incubated for about 48 hours, and the SARS-CoV-2 Spike pseudotyped virions are collected. FIG. 1B illustrates production of the SARS-CoV-2-induced coagulopathy animal model by administration of SARS-CoV-2 Spike pseudotyped virions. Some of the physiological effects of such administration are summarized.

FIG. 2A shows images of lung sections from mice administered SARS-CoV-2 Spike pseudotyped virions (top two panels) compared with 'BALD' Env-deficient-HIV particles lacking Spike. The two left panels were stained with a labeled anti-Mac-2 antibody to detect macrophages, while the two right panels were stained with anti-Gp91-phox antibodies to detect oxidative stress. FIG. 2B graphically illustrates the number of macrophages per field in the lungs of mice administered SARS-CoV-2 Spike pseudotyped virions and 'BALD' Env-deficient-HIV particles lacking Spike. FIG. 2C graphically illustrates the number Gp91-phox$^+$ cells per field, where expression of Gp91-phox is a marker for oxidative stress.

FIG. 3A shows images of lung sections of mice administered Spike-containing virions (bottom panel) and mice administered non-infective, 'BALD' virions that have no Spike proteins (top panel). The lung sections were both stained with labeled anti-fibrin and with anti-SARS-CoV-2 Spike antibodies. FIG. 3B shows higher magnification images of lung sections of mice administered Spike pseudotyped virions stained with labeled anti-fibrin and anti-Spike antibodies. As illustrated, the fibrin and Spike proteins are co-localized.

FIG. 4A is an image of a brain section from a mouse administered 'BALD' virions followed by staining with labeled anti-fibrin antibodies. FIG. 4B is an image of a brain section from a mouse administered Spike pseudotyped virions, where the brain section was stained with labeled anti-fibrin antibodies.

FIG. 5A shows a lung section from a wild type mouse that had been administered Spike pseudotyped virions followed by staining with labeled anti-Mac-2 and anti-Gp91-phox antibodies to detect macrophage infiltration and oxidative stress, respectively. As illustrated the macrophage infiltration and oxidative stress substantially co-localize. FIG. 5B shows a lung section from a fibrinogen-gene-knockout mouse administered Spike pseudotyped virions and then stained with anti-Mac-2 and anti-Gp91-phox antibodies to detect macrophage infiltration and oxidative stress respectively. As illustrated, little oxidative stress/inflammation is detected when fibrinogen is not expressed in these lung sections.

FIG. 7A-7C illustrate the effects of 5B8 anti-fibrin(ogen) antibody or IgG2b (control) antibody treatment on fibrin(ogen) deposits and Spike accumulation in mice injected with SARS-CoV-2 Spike-pseudotyped virions. FIG. 7A shows confocal micrograph images of immunofluorescence double immunostained mouse lung sections from SARS-CoV-2 Spike pseudovirion-injected mice at 24 hours after IgG2b (30 mg/kg) (left panel) or 5B8 (30 mg/kg) (right panel) intravenous administration. Immunoreactivity of spike is brighter (red in the original) while immunoreactivity of fibrin(ogen) is bright (green in the original) with concentrated deposits indicated by white arrows. Nuclei were stained with 4',6-diamidino-2-phenylindole (DAPI;). Scale bars, 200 µm. Representative images are shown from n=6 mice per group. FIG. 7B graphically illustrates the quantify of SARS-CoV-2 Spike deposition in mouse lung challenged by SARS-CoV-2 Spike pseudotyped virions for 24 h after 5B8 antibody (30 mg/kg) or IgG2b antibody (30 mg/kg) intravenous treatment. FIG. 7C graphically illustrates the quantify of fibrin(ogen) deposition in mouse lung challenged by SARS-CoV-2 Spike pseudotyped virions for 24 hours after 5B8 antibody (30 mg/kg) or IgG2b antibody (30 mg/kg) intravenous treatment. Data are from n=6 mice per group (mean±s.e.m.). **p<0.01 (two-tailed Mann-Whitney test).

FIG. 8 illustrates that SARS-CoV-2 Spike pseudotyped virions may increase fibrin-related brain inflammation. Photomicrographs are shown of brain sections after control or stereotaxic co-injection of fibrinogen with PBS, BALD, or Spike PVs. Allograft inflammatory factor 1 (Iba-1) immunoreactivity was detected as shown. Scale bar, 50 µm. The percent area of immunoreactivity in brain sections is quantified in the graph to the right for mice treated as indicated along the x-axis. Data are from n=6 mice per group (mean±s.e.m.). *P<0.05, *P<0.001, **P<00001 (one-way ANOVA with Tukey's multiple comparisons test). n.s., not significant.

DETAILED DESCRIPTION

Described herein are animal models of the acute and long-term clotting and inflammatory complications of SARS-CoV-2 infection, and methods of using an animal model to identify therapeutic agents that can reduce or eliminate these complications. The animal model involves administration of virions pseudotyped with SARS-CoV-2 Spike protein. The physiological effects of such pseudotyped SARS-CoV-2 Spike protein expressing virions in the animal model are similar to the symptoms observed in humans infected with SARS-CoV-2 including inflammation and oxidative stress in organs such as the lungs, heart and brain; disruption of the blood brain barrier increased clot formation; and deposition of fibrin in the lungs, brain and heart.

It is surprising that mice administered pseudotyped virions, where the pseudotyped virions express only the Spike protein of SARS-CoV-2, demonstrated physiological effects similar to those observed in humans, because for example, while mice express ACE2 receptors, which are the receptors bound by SARS-CoV-2 Spike protein in humans, the SARS-CoV-2 Spike protein does not bind to the mouse version of ACE2.

Pseudotyping

A pseudotyped virus (PV) is a virus particle with an envelope protein originating from a different virus. In general, a virus includes two components: structural proteins and a genome. The genome (DNA or RNA) provides the genetic information required for viral reproduction and synthesis of the structural proteins. The structural proteins surround the genome. These two components, the genome and the structural proteins, are assembled into virions in the late stages of infection in a cell.

Pseudotyped viruses are generally constructed as infectious but non-replicating viruses by providing cells with an expression vector encoding the Envelope/Spike proteins in trans with an HIVΔEnv provirus expression vector. The cells selected for receiving these expression vectors should be able to produce virions. The pseudotyped virions so produced will contain a new Env/Spike protein on the surface of the virion but these new viruses will only be able to support a single round of entry and expression. This approach avoids the construction chimeric viruses with new cellular tropism and potentially enhanced pathogenicity.

Figure 1A:
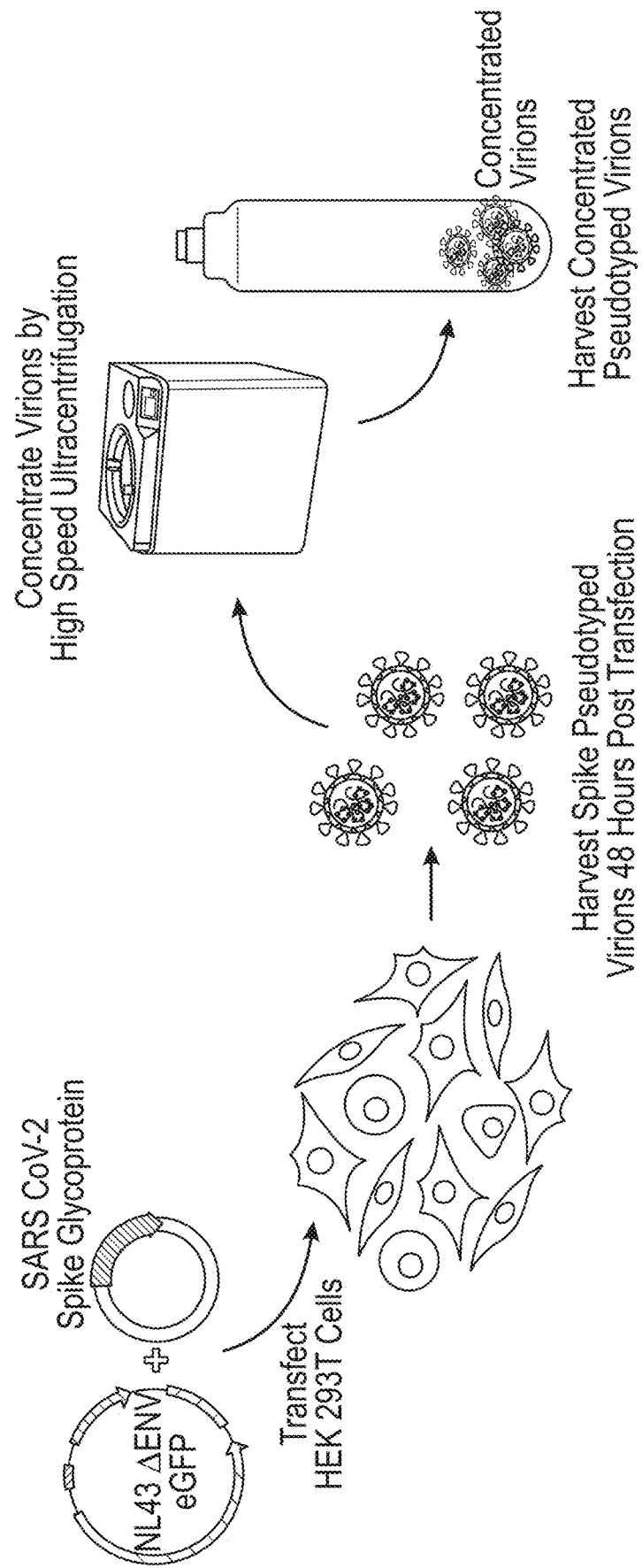
FIG. 1A-1B illustrate production of the SARS-CoV-2 Spike pseudotyped virions and methods by which the SARS-CoV-2-induced coagulopathy animal model was made.

For pseudotyping HIVΔEnv virions with SARS-CoV-2 Spike (FIG. 1A). 293 T cells are transfected with expression vectors encoding NL4-3 HIVΔEnv (carrier expression cassette/vector) and a second expression vector encoding a SARS-CoV-2 Spike protein. As a control, "bald" virions can be produced where the SARS-CoV-2 Spike vector is not cotransfected into the cells. When both of the carrier and the SARS-CoV-2 Spike-encoding vectors are present in a cell, pseudotyped viral particles are produced that display the SARS-CoV-2 Spike protein allowing entry of the pseudotyped virions via the receptors utilized by SARS-CoV-2 Spike protein. These virions can be concentrated by ultracentrifugation (FIG. 1A). In initial experiments, animals were intravenously injected with pseudotyped virions containing about 100 ng of p24 Gag (the capsid protein encoded by HIV). However, to model acute SARS-CoV-2 infection, pseudotyped virions in amounts ranging between about 1 ng to 10,000 ng HIV p24Gag can be injected. To model Long Covid, pseudotyped virions in amounts ranging between 0.01-1 ng HIV p24Gag can be injected weekly.

Animals are generally analyzed for pathologic changes at about 24 hours after administration of the pseudotyped virions. The animals can also be evaluated over days or weeks. In studies aimed at exploring potential role of Spike and fibrin deposition in Long COVID, the animals can be evaluated over time, for example, over several Weeks or several months.

The carrier expression cassette/vector and the SARS-CoV-2 Spike protein-encoding vector can include cis-acting sequences for expressing the encoded proteins and in some cases the nucleic acids. The pseudotyping carrier vector and the SARS-CoV-2 Spike protein-encoding vector can have the same or different types of promoter and other regulatory sequences. In some cases, the promoters can be selected to generate sufficient Spike protein for display on the majority or substantially all viral particles.

The coding sequences and cis-acting sequences of the carrier may come from the carrier virus alone or the carrier virus genome may be modified to include heterologous elements (e.g., a packaging sequence, a promoter) from other sources, which may be naturally occurring or partially or completely synthetic. For example, some sequences can be derived from a closely related virus within the same or a different viral genus. To illustrate, if the carrier includes a modified RNA virus genome such as a modified lentiviral virus genome, some sequences (e.g., 5' and/or 3' UTR, promoters, etc.) can be derived from another lentivirus.

In some cases the carrier virus can include modified alphavirus, rhabdovirus or lentivirus viral sequences that do not include the viral envelope sequences. In some cases, the carrier can be a HIV-delta Env packaging vector (e.g., an proviral DNA lacking its natural Env gene).

The carrier can also express a reporter molecule that provides a detectable signal. Such a reporter molecule can be a fluorescent or luminescent molecule that is detectable by microscopy. One example, of a useful carrier that express a green protein fluorescent protein is the HIV-1 NL4-3 ΔEnv EGFP Reporter Vector (see hivreagentprogram.org catalog no. ARP-11100).

SARS-CoV-2 Spike Protein

As described herein, an Animal Model of SARS-CoV-2 can readily be prepared and used by administering pseudotyped virions that display SARS-CoV-2 Spike proteins on the surface of the pseudotyped viruses.

The Spike protein is responsible for facilitating entry of the SAKS-CoV-2 into cells. It is composed of a short intracellular tail, a transmembrane anchor, and a large ectodomain that consists of a receptor binding S1 subunit and a membrane-fusing S2 subunit. The SARS-CoV-2 Spike protein binds viral particles to angiotensin II converting enzyme (ACE2) receptors on the surface of target cells and facilitates viral entry into cells. A variety of Spike proteins can be used in the pseudotyped virions and in the Animal Models described herein.

One example of a SARS-CoV-2 Spike protein sequence is shown below as SEQ ID NO:1.

```
  1   MFVFLVLLPL VSSQCVNLTT RTQLPPAYTN SFTRGVYYPD
 41   KVFRSSVLHS TQDLFLPFFS NVTNFHAIHV SGTNGTKRFD
 81   NPVLPFNDGV YFASTEKSNI IRGWIFGTTL DSKTQSLLIV
121   NNATNVVIKV CEFQFCNDPF LGVYYHKNNK SWMESEFRVY
161   SSANNCTFEY VSQPFLMDLE GKQGNFKNLR EFVFKNIDGY
201   FKIYSKHTPI NLVRDLPQGF SALEPLVDLP IGINITRFQT
241   LLALHRSYLT PGDSSSGWTA GAAAYYVGYL QPRTFLLKYN
281   ENGTITDAVD CALDPLSETK CTLKSFTVEK GIYQTSNFRV
321   QPTESIVRFP NITNLCPFGE VFNATRFASV YAWNRKRISN
361   CVADYSVLYN SASFSTFKCY GVSPTKLNDL CFTNVYADSF
401   VIRGDEVRQI APGQTGKIAD YNYKLPDDFT GCVIAWNSNN
441   LDSKVGGNYN YLYRLFRKSN LKPFERDIST EIYQAGSTPC
481   NGVEGFNCYF PLQSYGFQPT NGVGYQPYRV VVLSFELLHA
521   PATVCGPKKS TNLVKNKCVN FNFNGLTGTG VLTESNKKFL
561   PFQQFGRDIA DTTDAVRDPQ TLEILDITPC SFGGVSVITP
601   GTNTSNQVAV LYQDVNCTEV PVAIHADQLT PTWRVYSTGS
641   NVFQTRAGCL IGAEHVNNSY ECDIPIGAGI CASYQTQTNS
681   PRRARSVASQ SIIAYTMSLG AENSVAYSNN SIAIPTNFTI
721   SVTTEILPVS MTKTSVDCTM YICGDSTECS NLLLQYGSFC
761   TQLNRALTGI AVEQDKNTQE VFAQVKQIYK TPPIKDFGGF
801   NFSQILPDPS KPSKRSFIED LLFNKVTLAD AGFIKQYGDC
841   LGDIAARDLI CAQKFNGLTV LPPLLTDEMI AQYTSALLAG
881   TITSGWTFGA GAALQIPFAM QMAYRFNGIG VTQNVLYENQ
921   KLIANQFNSA IGKIQDSLSS TASALGKLQD VVNQNAQALN
961   TLVKQLSSNF GAISSVLNDI LSRLDKVEAE VQIDRLITGR
1001  LQSLQTYVTQ QLIRAAEIRA SANLAATKMS ECVLGQSKRV
1041  DFCGKGYHLM SFPQSAPHGV VFLHVTYVPA QEKNFTTAPA
1081  ICHDGKAHFP REGVFVSNGT HWFVTQRNFY EPQIITTDNT
1121  FVSGNCDVVI GIVNNTVYDP LQPELDSFKE ELDKYFKNHT
1161  SPDVDLGDIS GINASVVNIQ KEIDRLNEVA KNLNESLIDL
1201  QELGKYEQYI KWPWYIWLGF IAGLIAIVMV TIMLCCMTSC
1241  CSCLKGCCSC GSCCKFDEDD SEPVLKGVKL HYT
```

A receptor binding S1 subunit can reside at amino acid positions 330-583 of the SEQ ID NO:1 spike protein (shown below as SEQ ID NO:2).

```
330                   P NITNLCPFGE VFNATRFASV YAWNRKRISN
361   CVADYSVLYN SASFSTFKCY GVSPTKLNDL CFTNVYADSF
401   VIRGDEVRQI APGQTGKIAD YNYKLPDDFT GCVIAWNSNN
441   LDSKVGGNYN YLYRLFRKSN LKPFERDIST EIYQAGSTPC
481   NGVEGFNCYF PLQSYGFQPT NGVGYQPYRV VVLSFELLHA
521   PATVCGPKKS TNLVKNKCVN FNFNGLTGTG VLTESNKKFL
561   PFQQFGRDIA DTTDAVRDPQ TLE
```

The SARS-CoV-2 spike protein membrane-fusing S2 domain may be at positions 662-1270 of the SEQ ID NO:5 spike protein (shown below as SEQ ID NO:3).

662 CDIPEGAGI CASYQTQTNS

681 PRRARSVASQ SIIAYTMSLG AENSVAYSNN SIAIPTNFTI

721 SVTTEILPVS MTKTSVDCTM YICGDSTECS NLLLQYGSFC

761 TQLNRALTGI AVEQDKNTQE VFAQVKQIYK TPPIKDFGGF

801 NFSQELPDPS KPSKRSFIED LLFNKVTLAD AGFIKQYGDC

841 LGDIAARDLI CAQKFNGLTV LPPLLTDEMI AQYTSALLAG

881 TITSGWTFGA GAALQIPFAM QMAYRFNGIG VTQNVLTENQ

921 KLIANQFNSA IGKIQDSLSS TASALGKLQD VVNQNAQALN

961 TLVKQLSSNF GAISSVLNDI LSRLDKVEAE VQIDRLITGR

1001 LQSLQTYVTQ QLIRAAEIRA SANLAATKMS ECVLGQSKRV

1041 DFCGKGYHLM SFPQSAPHGV VFLHVTYVPA QEKNFTTAPA

1081 ICHDGKAHFP REGVFVSNGT HWFVTQRNFY EPQIITTDNT

1121 FVSGNCDVVI GIVNNTVYDP LQPELDSFKE ELDKYFKNHT

1161 SPDVDLGDIS GINASVVNIQ KEIDRLNEVA KNLNESLIDL

1201 QELGKYEQYI KWPWYIWLGF IAGLIAIVMV TIMLCCMTSC

1241 CSCLKGCCSC GSCCKFDEDD SPEVLKGVKL H

Other types of SARS-CoV-2 Spike proteins can be used in the animal model and in the methods described herein, including any available SARS-CoV-2 Spike mutant or variant proteins.

For example, the following is a SARS-CoV-2 Spike protein sequence with a somewhat longer sequence (highlighted) than the foregoing SEQ ID NO:1 Spike protein sequence. The following SARS-CoV-2 Spike protein sequence has NCBI Accession No. BCN86353.1 (SEQ ID NO:4).

1 MFLLTTKRTM FVFLVLLPLV SSQCVNLTTR TQLPPAYTNS

41 FTRGVYYPDK VFRSSVLHST QDLFLPFFSN VTWFHAIHVS

81 GTNGTKRFDN PVLPFNDGVY FASTEKSNII RGWIFGTTLD

121 SKTQSLLIVN NATNVVIKVC EFQFCNDPFL GVYYHKNNKS

161 WMESEFRVYS SANNCTFEYV SQPFLMDLEG KQGNFKNLRE

201 FVFKNIDGYF KIYSKHTPIN LVRDLPQGFS ALEPLVDLPI

241 GINITRFQTL LALHRSYLTP GDSSSGWTAG AAAYYVGYLQ

281 PRTFLLKYNE NGTITDAVDC ALDPLSETKC TLKSFTVEKG

321 IYQTSNFRVQ PTESIVRFPN ITNLCPFGEV FNATRFASVY

361 AWNRKRISNC VADYSVLYNS ASFSTFKCYG VSPTKLNDLC

401 FTNVYADSFV IRGDEVRQIA PGQTGKIADY NYKLPDDFTG

441 CVIAWNSNNL DSKVGGNYNY LYRLFRKSNL KPFERDISTE

481 IYQAGSTPCN GVEGFNCYFP LQSYGFQPTN GVGYQPYRVV

521 VLSFELLHAP ATVCGPKKST NLVKNKCVNF NFNGLTGTGV

561 LTESNKKFLP FQQFGRDIAD TTDAVRDPQT LEILDITPCS

-continued

601 FGGVSVITPG TNTSNQVAVL YQDVNCTEVP VAIHADQLTP

641 TWRVYSTGSN VFQTRAGCLI GAEHVNNSYE CDIPIGAGIC

681 ASYQTQTNSP RRARSVASQS IIAYTMSLGA ENSVAYSNNS

721 IAIPTNFTIS VTTEILPVSM TKTSVDCTMY ICGDSTECSN

761 LLLQYGSFCT QLNRALTGIA VEQDKNTQEV FAQVKQIYKT

801 PPIKDFGGFN FSQILPDPSK PSKRSFIEDL LFNKVTLADA

841 GFIKQYGDCL GDIAARDLIC AQKFNGLTVL PPLLTDEMIA

881 QYTSALLAGT ITSGWTFGAG AALQIPFAMQ MAYRFNGIGV

921 TQNVLYENQK LIANQFNSAI GKIQDSLSST ASALGKLQDV

961 VNQNAQALNT LVKQLSSNFG AISSVLNDIL SRLDKVEAEV

1001 QIDRLITGRL QSLQTYVTQQ LIRAAEIRAS ANLAATKMSE

1041 CVLGQSKRVD FCGKGYHLMS FPQSAPHGVV FLHVTYVPAQ

1081 EKNFTTAPAI CHDGKAHFPR EGVFVSNGTH WFVTQRNFYE

1121 PQIITTDNTF VSGNCDVVIG IVNNTVYDPL QPELDSFKEE

1161 LDKYFKNHTS PDVDLGDISG INASVVNIQK EIDRLNEVAK

1201 NLNESLIDLQ ELGKYEQYIK WPWYIWLGFI AGLIAIVMVT

1241 IMLCCMTSCC SCLKGCCSCG SCCKFDEDDS EPVLKGVKLH

1281 YT

In another example, the following is a SARS-CoV-2 Spike protein sequence with a point mutation at about position 486 (highlighted below) compared to the foregoing SEQ ID NO:1 Spike protein sequence. The following SARS-CoV-2 Spike protein sequence has NCBI Accession No. QJS39567.1. (SEQ ID NO:5).

1 MFVFLVLLPL VSSQCVNLTT RTQLPPAYTN SFTRGVYYPD

41 KVFRSSVLHS TQDLFLPFFS NVTWFHAIHV SGTNGTKRFD

81 NPVLPFNDGV YFASTEKSNI IRGWIFGTTL DSKTQSLLIV

121 NNATNVVIKV CEFQFCNDPF LGVYYHKNNK SWMESEFRVY

161 SSANNCTFEY VSQPFLMDLE GKQGNFKNLR EFVFKNIDGY

201 FKIYSKHTPI NLVRDLPQGF SALEPLVDLP IGINITRFQT

241 LLALHRSYLT PGDSSSGWTA GAAAYYVGYL QPRTFLLKYN

281 ENGTITDAVD CALDPLSETK CTLKSFTVEK GIYQTSNFRV

321 QPTESIVRFP NITNLCPFGE VFNATRFASV YAWNRKRISN

361 CVADYSVLYN SASGSTFKCY GVSPTKLNDL CFTNVYADSF

401 VIRGDEVRQI APGQTGKIAD YNKKLPDDFT GCVIAWNSNN

441 LDSKVGGNYN YLYRLFRKSN LKPFERDIST EIYQAGSTPC

481 KGVEGLNCYF PLQSYGFQPT NGVGYQPYRV VVLSFELLHA

521 PATVCGPKKS TNLVKNKCVN FNFNGLTGTG VLTESNKKFL

561 PFQQFGRDIA DTTDAVRDPQ TLEILDITPC SFGGVSVITP

601 GTNTSNQVAV LYQDVNCTEV PVAIHADQLT PTWRVYSTGS

641 NVFQTRAGCL IGAEHVNNSY ECDIPIGAGI CASYQTQTNS

```
 681 PRRARSVASQ SIIAYTMSLG AENSVAYSNN SIAIPTNFTI

721 SVTTEILPVS MTKTSVDCTM YICGDSTECS NLLLQYGSFC

761 TQLNRALTGI AVEQDKNTQE VFAQVKQIYK TPPIKDFGGF

801 NFSQILPDPS KPSKRSFIED LLFNKVTLAD AGFIKQYGDC

841 LGDIAARDLI CAQKFNGLTV LPPLLTDEMI AQYTSALLAG

881 TITSGWTFGA GAALQIPFAM QMAYRFNGIG VTQNVLYENQ

921 KLIANQFNSA IGKIQDSLSS TASALGKLQD VVNQNAQALN

961 TLVKQLSSNF GAISSVLNDI LSRLDKVEAE VQIDRLITGR

1001 LQSLQTYVTQ QLIRAAEIRA SANLAATKMS ECVLGQSKRV

1041 DFCGKGYHLM SFPQSAPHGV VFLHVTYVPA QEKNFTTAPA

1081 ICHDGKAHFP REGVFVSNGT HWFVTQRNFY EPQIITTDNT

1121 FVSGNCDVVI GIVNNTVYDP LQPELDSFKE ELDKYFKNHT

1161 SPDVDLGDIS GINASVVNIQ KEIDRLNEVA KNLNESLIDL

1201 QELGKYEQYI KWPWYIWLGF IAGLIAIVMV TIMLCCMTSC

1241 CSCLKGCCSC GSCCKFDEDD SEPVLKGVKL HYT
```

In another example, the following is a SARS-CoV-2 Spike protein sequence with a point mutation at about position 22 (highlighted below) compared to the foregoing SEQ ID NO:1 Spike protein sequence. The following SARS-CoV-2 Spike protein sequence has NCBI Accession No. QJX45031.1 (SEQ ID NO:6).

```
   1 MFVFLVLLPL VSSQCVNLTT RAQLPPAYTN SFTRGVYYPD

41 KVFRSSVLHS TQDLFLPFFS NVTWFHAIHV SGTNGRKRFD

81 NPVLPFNDGV YFASTEKSNI IRGWIFGTTL DSKTQSLLIV

121 NNATNVVIKV CEFQFCNDPF LGVYYHKNNK SWMESEFRVY

161 SSANNCTFEY VSQPFLMDLE GKQGNFKNLR EFVFKNIDGY

201 FKIYSKHTPI NLVRDLPQGF SALEPLVDLP IGINITRFQT

241 LLALHRSYLT PGDSSSGWTA GAAAYYVGYL QPRTFLLKYN

281 ENGTITDAVD CALDPLSETK CTLKSFTVEK GIYQTSNFRV

321 QPTESIVRFP NITNLCPFGE VFNATRFASV YAWNRKRISN

361 CVADYSVLYN SASFSTFKCY GVSPTKLNDL CFTNVYADSF

401 VIRGDEVRQI APGQTGKIAD YNYKLPDDFT GCVIAWNSNN

441 LDSKVGGNYN YLYRLFRKSN LKPFERDIST EIYQAGSTPC

481 NGVEGFNCYF PLQSYGFQPT NGVGYQPYRV VVLSFELLHA

521 PATVCGPKKS TNLVKNKCVN FNFNGLTGTG VLTESNKKFL

561 PFQQFGRDIA DTTDAVRDPQ TLEILDITPC SFGGVSVITP

601 GTNTSNQVAV LYQDVNCTEV PVAIHADQLT PTWRVYSTGS

641 NVFQTRAGCL IGAEHVNNSY ECDIPIGAGI CASYQTQTNS

681 PRRARSVASQ SIIAYTMSLG AENSVAYSNN SIAIPTNFTI

721 SVTTEILPVS MTKTSVDCTM YICGDSTECS NLLLQYGSFC

761 TQLNRALTGI AVEQDKNTQE VFAQVKQIYK TPPIKDFGGF

801 VFSQILPDPS KPSKRSFIED LLFNKVTLAD AGFIKQYGDC

841 LGDIAARDLI CAQKFNGLTV LPPLLTDEMI AQYTSALLAG

881 TITSGWTFGA GAALQIPFAM QMAYRFNGIG VTQNVLYENQ

921 KLIANQFNSA IGKIQDSLSS TASALGKLQD VVNQNAQALN

961 TLVKQLSSNF GAISSVLNDI LSRLDKVEAE VQIDRLITGR

1001 LQSLQTYVTQ QLIRAAEIRA SANLAATKMS ECVLGQSKRV

1041 DFCGKGYHLM SFPQSAPHGV VFLHVTYVPA QEKNFTTAPA

1081 ICHDGKAHFP REGVFVSNGT HWFVTQRNFY EPQIITTDNT

1121 FVSGNCDVVI GIVNNTVYDP LQPELDSFKE ELDKYFKNHT

1161 SPDVDLGDIS GINASVVNIQ KEIDRLNEVA KNLNESLIDL

1201 QELGKYEQYI KWPWYIWLGF IAGLIAIVMV TIMLCCMTSC

1241 CSCLKGCCSC GSCCKFDEDD SEPVLKGVKL HYT
```

In another example, the following is another SARS-CoV-2 Spike protein sequence with a point mutation at about position 22 (highlighted below) compared to the foregoing SEQ ID NO:1 Spike protein sequence. The following SARS-CoV-2 Spike protein sequence has NCBI Accession No. QJQ84843.1 (SEQ ID NO:7).

```
   1 MFVFLVLLPL VSSQCVNLTT RIQLPPAYTN SFTRGVYYPD

41 KVFRSSVLHS TQDLFLPFFS NVTWFHAIHV SGTNGTKRFD

81 NPVLPFNDGV YFASTEKSNI IRGWIFGTTL DSKTQSLLIV

121 NNATNVVIKV CEFQFCNDPF LGVYYHKNNK SWMESEFRVY

161 SSANNCTFEY VSQPFLMDLE GKQGNFKNLR EFVFKNIDGY

201 FKIYSKHTPI NLVRDLPQGF SALEPLVDLP IGINITRFQT

241 LLALHRSYLT PGDSSSGWTA GAAAYYVGYL QPRTFLLKYN

281 ENGTITDAVD CALDPLSETK CTLKSFTVEK GIYQTSNFRV

321 QPTESIVRFP NITNLCPFGE VFNATRFASV YAWNRKRISN

361 CVADYSVLYN SASFSTFKCY GVSPTKLNDL CFTNVYADSF

401 VIRGDEVRQI APGQTGKIAD YNYKLPDDFT GCVIAWNSNN

441 LDSKVGGNYN YLYRLFRKSN KLPFERDIST EIYQAGSTPC

481 NGVEGFNCYF PLQSYGFQPT NGVGYQPYRV VVLSFELLHA

521 PATVCGPKKS TNLVKNKCVN FNFNGLTGTG VLTESNKKFL

561 PFQQFGRDIA DTTDAVRDPQ TLEILDITPC SFGGVSVITP

601 GTNTSNQVAV LYQDVNCTEV PVAIHADQLT PTWRVYSTGS

641 NVFQTRAGCL IGAEHVNNSY ECDIPIGAGI CASYQTQTNS

681 PRRARSVASQ SIIAYTMSLG AENSVAYSNN SIAIPTNFTI

721 SVTTEILPVS MTKTSVDCTM YICGDSTECS NLLLQYGSFC

761 TQLNRALTGI AVEQDKNTQE VFAQVKQIYK TPPIKDFGGF

801 NFSQILPDPS KPSKRSFIED LLFNKVTLAD AGFIKQYGDC

841 LGDIAARDLI CAQKFNGLTV LPPLLTDEMI AQYTSALLAG

881 TITSGWTFGA GAALQIPFAM QMAYRFNGIG VTQNVLYENQ

921 KLIANQFNSA IGKIQDSLSS TASALGKLQD VVNQNAQALN
```

```
 960  TLVKQLSSNF GAISSVLNDI LSRLDKVEAE VQIDRLITGR
1001  LQSLQTYVTQ QLIRAAEIRA SANLAATKMS ECVLGQSKRV
1041  DFCGKGYHLM SFPQSAPHGV VFLHVTYVPA QEKNFTTAPA
1081  ICHDGKAHFP REGVFVSNGT HWFVTQRNFY EPQIITTDNT
1121  FVSGNCDVVI GIVNNTVYDP LQPEDLSFKE ELDKYFKNHT
1161  SPDVDLGDIS GINASVVNIQ KEIDRLNEVA KNLNESLIDL
1201  QELGKYEQYI KWPWYIWLGF IAGLIAIVMV TIMLCCMTSC
1241  CSCLKGCCSC GSCCKFDEDD SEPVLKGVKL HYT
```

In another example, the following is a SARS-CoV-2 Spike protein sequence with a point mutation at about position 157 (highlighted below) compared to the foregoing SEQ ID NO:1 Spike protein sequence. The following SARS-CoV-2 Spike protein sequence has NCBI Accession No. QII57278.1 (SEQ ID NO:8).

```
   1  MFVFLVLLPL VSSQCVNLTT RTQLPPAYTN SFTRGVYYPD
  41  KVFRSSVLHS TQDLFLPFFS NVTWFHAIHV SGTNGTKRFD
  81  NPVLPFNDGV YFASTEKSNI IRGWIFGTTL DSKTQSLLIV
 121  NNATNVVIKV CEFQFCNDPF LGVYYHKNNK SWMESELRVY
 161  SSANNCTFEY VSQPFLMDLE GKQGNFKNLR EFVFKNIDGY
 201  FKIYSKHTPI NLVRDLPQGF SALEPLVDLP IGINITRFQT
 241  LLALHRSYLT PGDSSSGWTA GAAAYYVGYL QPRTFLLKYN
 281  ENGTITDAVD CALDPLSETK CTLKSFTVEK GIYQTSNFRV
 321  QPTESIVRFP NITNLCPFGE VFNATRFASV YAWNRKRISN
 361  CVADYSVLYN SASFSTFKCY GVSPTKLNDL CFTNVYADSF
 401  VIRGDEVRQI APGQTGKIAD YNYKLPDDFT GCVIAWNSNN
 441  LDSKVGGNYN YLYRLFRKSN LKPFERDIST EIYQAGSTPC
 481  NGVEGFNCYF PLQSYGFQPT NGVGYQPYRV VVLSFELLHA
 521  PATVCGPKKS TNLVKNKCVN FNFNGLTGTG VLTESNKKFL
 561  PFQQFGRDIA DTTDAVRDPQ TLEILDITPC SFGGVSVITP
 601  GTNTSNQVAV LYQDVNCTEV PVAIHADQLT PTWRVYSTGS
 641  NVFQTRAGCL IGAEHVNNSY ECDIPIGAGI CASYQTQTNS
 681  PRRARSVASQ SIIAYTMSLG AENSVAYSNN SIAIPTNFTI
 721  SVTTEILPVS MTKTSVDCTM YICGDSTECS NLLLQYGSFC
 761  TQLNRALTGI AVEQDKNTQE VFAQVKQIYK TPPIKDFGGF
 801  NFSQILPDPS KPSKRSFIED LLFNKVTLAD AGFIKQYGDC
 841  LGDIAARDLI CAQKFNGLTV LPPLLTDEMI AQYTSALLAG
 881  TITSGWTFGA GAALQIPFAM QMAYRFNGIG VTQNVLYENQ
 921  KLIANQFNSA IGKIQDSLSS TASALGKLQD VVNQNAQALN
 961  TLVKQLSSNF GAISSVLNDI LSRLDKVEAE VQIDRLITGR
1001  LQSLQTYVTQ QLIRAAEIRA SANLAATKMS ECVLGQSKRV
1041  DFCGKGYHLM SFPQSAPHGV VFLHVTYVPA QEKNFTTAPA
1081  ICHDGKAHFP REFVGVSNGT HWFVTQRNFY EPQIITTDNT
1121  FVSGNCDVVI GIVNNTVYDP LQPEDLSFKE ELDKYFKNHT
1161  SPDVDLGDIS GINASVVNIQ KEIDRLNEVA KNLNESLIDL
1201  QELGKYEQYI KWPWYIWLGF IAGLIAIVMV TIMLCCMTSC
1241  CSCLKGCCSC GSCCKFDEDD SEPVLKGVKL HYT
```

In another example, the following is a SARS-CoV-2 Spike protein sequence with a point mutation at about position 614 (highlighted below) compared to the foregoing SEQ ID NO:1 Spike protein sequence. The following SARS-CoV-2 Spike protein sequence has NCBI Accession No. 7KRQ_A (SEQ ID NO:9).

```
   1  MFVFLVLLPL VSSQCVNLTT RTQLPPAYTN SFTRGVYYPD
  41  KVFRSSVLHS TQDLFLPFFS NVTWFHAIHV SGTNGTKRFD
  81  KPVLPFNDGV YFASTEKSNI IRGWIFGTTL DSKTQSLLIV
 121  NNATNVVIKV CEFQFCNDPF LGVYYHKNNK SWMESEFRVY
 161  SSANNCTFEY VSQPFLMDLE GKQGNFKNLR EFVFKNIDGY
 201  FKIYSKHTPI NLVRDLPQGF SALEPLVDLP IGINITRFQT
 241  LLALHRSYLT PGDSSSGWTA GAAAYYVGYL QPRTFLLKYN
 281  ENGTITDAVD CALDPLSETK CTLKSFTVEK GIYQTSNFRV
 321  QPTESIVRFP NITNLCPFGE VFNATRFASV YAWNRKRISN
 361  CVADYSVLYN SASFSTFKCY GVSPTKLNDL CFTNVYADSV
 401  VIRDGEVRQI APGQTGKIAD YNYKLPDDFT GCVIAWNSNN
 441  LDSKVGGNYN YLYRLFRKSN LKPFERDIST EIYQAGSTPC
 481  NGVEGFNCYF PLQSYGFQPT NGVGYQPYRV VVLSFELLHA
 521  PATVCGPKKS TNLVKNKCVN FNFNGLTGTG VLTESNKKFL
 561  PFQQFGRDIA DTTDAVRDPQ TLEILDITPC SFGGVSVITP
 601  GTNTSNQVAV LYQGVNCTEV PVAIHADQLT PTWRVYSTGS
 641  NVFQTRAGCL IGAEHVNNSY ECDIPIGAGI CASYQTQTNS
 681  PRRARSVASQ SIIAYTMSLG AENSVAYSNN SIAIPTNFTI
 721  SVTTEILPVS MTKTSVDCTM YICGDSTECS NLLLQYGSFC
 761  TQLNRALTGI AVEQDKNTQE VFAQVKQIYK TPPIKDFGGF
 801  NFSQILPDPS NPSKRSFIED LLFNKVTLAD AGFIKQYGDC
 841  LGDIAARDLI CAQKFNGLTV LPPLLTDEMI AQYTSALLAG
 881  TITSGWTFGA GAALQIPFAM QMAYRFNGIG VTQNVLYENQ
 921  KLIANQFNSA IGKIQDSLSS TASALGKLQD VVNQNAQALN
 961  TLVKQLSSNF GAISSVLNDI LSRLDKVEAE VQIDRLITGR
1001  LQSLQTYVTQ QLIRAAEIRA SANLAATKMS ECVLGQSKRV
1041  DFCGKGYHLM SFPQSAPHGV VFLHVTYVPA QEKNFTTAPA
1081  ICHDGKAHFP REGVFVSNGT HWFVTQRNFY EPQIITTDNT
1121  FVSGNCDVVI GIVNNTVYDP LQPEDLSFKE ELDKYFKNHT
1161  SPDVDLGDIS GINASVVNIQ KEIDRLNEVA KNLNESLIDL
1201  QELGKYEQYI KWPWYIWLGF IAGLIAIVMV TIMLCCMTSC
```

```
1241 CSCLKGCCSC GSCCKFDEDD SEPVLKGVKL HYTLESGGGS

1281 AWSHPQFEKG GGSGGGSGGS SAWSHPQFEK
```

In another example, the following is a SARS-CoV-2 Spike protein sequence with a point mutation at about position 95 (highlighted below as an X, meaning any amino acid) compared to the foregoing SEQ ID NO:1 Spike protein sequence. The following SARS-CoV-2 Spike protein sequence has NCBI Accession No. QKU32813.1 (SEQ ID NO:10).

```
   1 MFVFLVLLPL VSSQCVNLTT RTQLPPAYTN SFTRGVYYPD

41 KVFRSSVLHS TQDLFLPFFS NVTWFHAIHV SGTNGTKRFD

81 NPVLPFNDGV YFASXEKSNI IRGWIFGTTL DSKTQSLLIV

121 NNATNVVIKV CEFQFCNDPF LGVYYHKNNK SWMESEFRVY

161 SSANNCTFEY VSQPFLMDLE GKQGNFKNLR EFVFKNIDGY

201 FKIYSKHTPI NLVRDLPQGF SALEPLVDLP IGINITRFQT

241 LLALHRSYLT PGDSSSGWTA GAAAYYVGYL QPRTFLLKYN

281 ENGTITDAVD CALDPLSETK CTLKSFTVEK GIYQTSNFRV

321 QPTESIVRFP NITNLCPFGE VFNATRFASV YAWNRKRISN

361 CVADYSVLYN SASFSTFKCY GVSPTKLNDL CFTNVYADSF

401 VIRGDEVRQI APGQTGKIAD YNYKLPDDFT GCVIAWNSNN

441 LDSKVGGNYN YLYRLFRKSN LKPFERDIST EIYQAGSTPC

481 NGVEGFNCYF PLQSYGFQPT NGVGYQPYRV VVLSFELLHA

521 PATVCGPKKS TNLVKNKCVN FNFNGLTGTG VLTESNKKFL

561 PFQQFGRDIA DTTDAVRDPQ TLEILDITPC SFGGVSVITP

601 GTGTSNQVAV LYQDVNCTEV PVAIHADQLT PTWRVYSTGS

641 NVFQTRAGCL IGAEHVNNSY ECDIPIGAGI CASYQTQTNS

681 PRRARSVASQ SIIAYTMSLG AENSVAYSNN SIAIPTNFTI

721 SVTTEILPVS MTKTSVDCTM YICGDSTECS NLLLQYGSFC

761 TQLNRALTGI AVEQDKNTQE VFAQVKQIYK TPPIKDFGGF

801 NFSQILPDPS KPSKRSFIED LLFNKVTLAD AGFIKQYGDC

841 LGDIAARDLI CAQKFNGLTV LPPLLTDEMI AQYTSALLAG

881 TITSGWTFGA GAALQIPFAM QMAYRFNGIG VTQNVLYENQ

921 KLIANQFNSA IGKIQDSLSS TASALGKLQD VVNQNAQALN

961 TLVKQLSSNF GAISSVLNDI LSRLDKVEAE VQIDRLITGR

1001 LQSLQTYVTQ QLIRAAEIRA SANLAATKMS ECVLGQSKRV

1041 DFCGKGYHLM SFPQSAPHGV VFLHVTYVPA QEKNFTTAPA

1081 ICHDGKAHFP REGVFVSNGT HWFVTQRNFY EPQIITTDNT

1121 FVSGNCDVVI GIVNNTVYDP LQPELDSFKE ELDKYFKNHT

1161 SPDVDLGDIS GINASVVNIQ KEIDRLNEVA KNLNESLIDL

1201 QELGKYEQYI KWPWYIWLGF IAGLIAIVMV TIMLCCMTSC

1241 CSCLKGCCSC GSCCKFDEDD SEPVLKGVKL HYT
```

In another example, the following is a SARS-CoV-2 Spike protein sequence with a point mutation at about position 547 (highlighted below) compared to the foregoing SEQ ID NO: 1 Spike protein sequence. The following SARS-CoV-2 Spike protein sequence has NCBI Accession No. QKS90791.1 (SEQ ID NO:11).

```
   1 MFVFLVLLPL VSSQCVNLTT RTQLPPAYTN SFTRGVYYPD

41 KVFRSSVLHS TQDLFLPFFS NVTWFHAIHV SGTNGTKRFD

81 NPVLPFNDGV YFASTEKSNI IRGWIFGTTL DSKTQSLLIV

121 NNATNVVIKV CEFQFCNDPE LGVYYHKNNK SWMESEFRVY

161 SSANNCTFEY VSQPFLMDLE GKQGNFKNLR EFVFKNIDGY

201 FKIYSKHTPI NLVRDLPQGF SALEPLVDLP IGINITRFQT

241 LLALHRSYLT PGDSSSGWTA GAAAYYVGYL QPRTFLLKYN

281 ENGTITDAVD CALDPLSETK CTLKSFTVEK GIYQTSNFRV

321 QPTESIVRFP NITNLCPFGE NFNATRFASV YAWNRKRISN

361 CVADYSVLYN SASFSTFKCY GVSPTKLNDL CFTNVYADSF

401 VIRGDEVRQI APGQTGKIAD YNYKLPDDFT GCVIAWNSNN

441 LDSKVGGNYN YLYRLFRKSN LKPFERDIST EIYQAGSTPC

481 NGVEGFNCYF PLQSYGFQPT NGVGYQPYRV VVLSFELLHA

521 PATVCGPKKS TNLVKNKCVN FNFNGLIGTG VLTESNKKFL

561 PFQQFGRDIA DTTDAVRDPQ TLEILDITPC SFGGVSVITP

601 GTGTSNQVAV LYQDVNCTEV PVAIHADQLT PTWRVYSTGS

641 NVFQTRAGCL IGAEHVNNSY ECDIPIGAGI CASYQTQTNS

681 PRRARSVASQ SIIAYTMSLG AENSVAYSNN SIAIPTNFTI

721 SVTTEILPVS MTKTSVDCTM YICGDSTECS NLLLQYGSFC

761 QTLNRALTGI AVEQDKNTQE VFAQVKQIYK TPPIKDFGGF

801 NFSQILPDPS KPSKRSFIED LLFNKVTLAD AGFIKQYGDC

841 LGDIAARDLI CAQKFNGLTV LPPLLTDEMI AQYTSALLAG

881 TITSGWTFGA GAALQIPFAM QMAYRFNGIG VTQNVLYENQ

921 KLIANQFNSA IGKIQDSLSS TASALGKLQD VVNQNAQALN

961 TLVKQLSSNF GAISSVLNDI LSRLDKVEAE VQIDRLITGR

1001 LQSLQTYVTQ QLIRAAEIRA SANLAATKMS ECVLGQSKRV

1041 DFCGKGYHLM SFPQSAPHGV VFLHVTYVPA QEKNFTTAPA

1081 ICHDGKAHFP REGVFVSNGT HWFVTQRNFY EPQIITTDNT

1121 FVSGNCDVVI GIVNNTVYDP LQPELDSFKE ELDKYFKNHT

1161 SPDVDLGDIS GINASVVNIQ KEIDRLNEVA KNLNESLIDL

1201 QELGKYEQYI KWPWYIWLGF IAGLIAIVMV TIMLCCMTSC

1241 CSCLKGCCSC GSCCKFDEDD SEPVLKGVKL HYT
```

As described herein a variety of isoforms and variants of SARS-CoV-2 Spike proteins can be used in the methods and compositions described herein. For example, the SARS-CoV-2 Spike proteins used in the methods and compositions described herein can have a sequence with between 55-100% sequence identity to any of the Spike protein sequences (reference sequences) described herein. In some cases, the SARS-CoV-2 Spike proteins used in the methods and compositions described herein can, for example, have at least 55% sequence identity, preferably 60%, preferably 70%, preferably 80%, preferably at least 90%, preferably at least 95%, preferably at least 96%, preferably at least 97% sequence, preferably at least 98%, preferably at least 99% identity to a reference sequence over a specified comparison window. Optimal alignment may be ascertained or conducted using the homology alignment algorithm of Needleman and Wunsch, J. Mol. Biol. 48:443-53 (1970).

Screening Methods

Most people who become infected with SARS-CoV-2 (COVID-19) recover completely within a few weeks. But some people experience a multitude of symptoms that can be life-threatening. Such symptoms of SARS-CoV-2 infection include inflammation, oxidative stress, fibrin deposition, clot formation, or a combination thereof in organs such as the lungs, heart and brain; disruption of the blood brain barrier; and, as illustrated herein increased clot formation and deposition of fibrin in the lungs, brain and heart.

The methods and animal models described herein facilitate screening of agents for treatment of the acute and long term symptoms of SARS-CoV-2 infection and can verify the efficacy of newly identified and routinely available agents for treating SARS-CoV-2 infections by SARS-CoV-2 mutants that have mutant Spike proteins.

The animal model can be generated by administering virions pseudotyped with SARS-CoV-2 Spike. Symptoms occurring in the animal model, such as clotting and inflammation can then be observed, measured and/or quantified. The symptoms can be observed, measured and/or quantified compared to a control animal who did not receive the pseudotyped SARS-CoV-2 Spike containing virions, compared to a control animal who received 'BALD' virions lacking Spike.

To screen for efficacious therapeutic agent, the test agents can be administered to the animal model to determine whether those test agents can ameliorate the physiological effects of the SARS-CoV-2 Spike pseudotyped virions. Such test agents can be administered at the same time as the SARS-CoV-2 Spike pseudotyped virions are administered or after the pseudotyped virions are administered.

The animal used in the model can be a rodent, For example, the animal can be a. mouse, rat, or hamster. in some cases, the animal is a thin-skulled animal (see, e.g., Yang et al. (Nat Protoc.5(2): 201-208 (February 2010)).

The symptoms and physiological effects of the SARS-CoV-2 Spike pseudotyped virions can be observed, measured or quantified in at least one of the organs of the animal. For example, the symptoms can be observed, measured or quantified in one or more of lungs, brains, hearts, blood vessels, gut, or a combination thereof.

Test agents that can be tested include, for example, small molecules, polypeptides, or antibody preparations. In some cases, the antibody preparations can be human antibodies or humanized antibodies, The inventors have discovered that anti-fibrin and anti-fibrinogen antibodies can inhibit the symptoms of SARS-CoV-2 infection, and that anti-fibrin antibodies can inhibit binding of SARS-CoV-2 Spike to fibrin. Hence, the test agent can be an anti-fibrin antibody, an anti-fibrinogen antibody, or an anti-SARS-CoV-2 protein antibody. In some cases, the test agent can be an anti-SARS-CoV-2 Spike antibody.

The SARS-CoV-2 symptoms can, for example, include inflammation, oxidative stress, fibrin deposition, dot formation, or a combination thereof. The methods can therefore include measuring decreases or increases in inflammation within the subject compared to the control. The methods can include measuring inflammation in tissues with fibrin deposition compared to the control. For example, the method can include measuring inflammation in the subject's lung, heart, brain, gut, blood vessels, or a combination thereof compared to the control.

The methods can also include measuring the extent to which the test agent can bind fibrin or a SARS-CoV-2 protein. For example, the methods can include measuring the extent to which the test agent can bind the SARS-CoV-2 Spike protein. The methods can also include measuring SARS-CoV-2 virus binding to fibrin or fibrinogen compared to the control. The methods can also include measuring SARS-CoV-2 Spike protein binding to fibrin or fibrinogen, The methods can also include measuring Mac-1 protein binding to fibrin or fibrinogen compared to the control. The methods can also include measuring whether inhibition of SARS-CoV-2 Spike protein binding, SARS-CoV-2 viral particle binding, or Mac-1 binding to the fibrin or fibrinogen is greater than 50% compared to the control. The methods can also include measuring whether binding to the fibrin or fibrinogen γC domain is inhibited compared to the control. The methods can also include measuring binding to a fibrin epitope with peptide sequence CKKTTMKIIPFNRLTIG (SEQ ID NO:12), Bβ$_{119-129}$ (YLLKDLWQKRQ, SEQ ID NO:13), γ$_{163-181}$ (QSGLYFPLKANQQFLVY; SEQ ID NO:14), and/or γ$_{364-395}$ (DNGIIWATWKTRWYSMKKTTMKIIPFNRLTIG; SEQ ID NO:15) compared to a control.

Fibrinogen/Fibrin

The inventors have determined that the Spike protein of SARS-CoV-2 binds fibrinogen and fibrin, and that antibodies directed against fibrin are surprisingly effective at reducing such binding as well as reducing the inflammation associated with SARS-CoV-2 infection. Fibrin is deposited in tissues of patients infected with SARS-CoV-2 including the lung, heart, and brain. Such fibrin deposition may contribute to the short- and long-term symptoms of SARS-CoV-2 infection. No current therapeutics prevent the fibrin-mediated effects inducing inflammation and thrombosis caused by SARS-CoV-2.

Fibrinogen (factor I) is a glycoprotein complex that is made in the liver and that circulates in the blood of vertebrates. During tissue and vascular injury, fibrinogen is converted enzymatically by thrombin to fibrin that can then form a fibrin-based blood clot to occlude blood vessels and stop bleeding. Fibrin can also bind and reduce the activity of thrombin (fibrin is sometimes referred to as antithrombin I), which limits clotting. Fibrin also mediates blood platelet and endothelial cell spreading, tissue fibroblast proliferation, capillary tube formation, and angiogenesis, Fibrin therefore can promote revascularization and wound healing. However, because SARS-CoV-2 binds to fibrin, excessive fibrin deposition can contribute to the symptoms of SARS-CoV-2 infection.

An example of a human fibrinogen sequence is the fibrinogen gamma chain isoform gamma-A precursor sequence (NCBI accession number NP_000500.2), provided as SEQ ID NO:16 below.

```
  1 MSWSLHPRNL ILYFYALLFL SSTCVAYVAT RDNCCILDER

41 FGSYCPTTCG IADFLSTYQT KVDKDLQSLE DILHQVENKT

81 SEVKQLIKAI QLTYNPDESS KPNMIDAATL KSRKMLEEIM

121 KYEASILTHD SSIRYLQEIY NSNNQKIVNL KEKVAQLEAQ

161 CQEPCKDTVQ IHDITGKDCQ DIANKGAKQS GLYFIKPLKA
```

```
201 NQQFLVYCEI DGSGNGWTVF QKRLDGSVDF KKNWIQYKEG

241 FGHLSPTGTT EFWLGNEKIH LISTQSAIPY ALRVELEDWN

281 GRTSTADYAM FKVGPEADKY RLTYAYFAGG DAGDAFDGFD

321 FGDDPSDKFF TSHNGMQFST WDNDNDKFEG NCAEQDGSGW

361 WMNKCHAGHL NGVYYQGGTY SKASTPNGYD NGIIWATWKT

401 RWYSMKKTTM KIIPFNRLTI GRGQQHHLGG AKQAGDV
```

Antibodies directed against the fibrin γ epitope, CKKTTMKIIPFNRLTIG (SEQ ID NO:12, highlighted above in the SEQ NO:3 sequence), are particularly effective at decreasing binding of the SARS-CoV-2 Spike protein to fibrin and to fibrinogen. However, the SARS-CoV-2 Spike protein can bind to the fibrin Bβ$_{119-129}$ (YLLKDLWQKRQ, SEQ ID NO:13), γ$_{163-181}$ (QSGLYFIKPLKANQQFLVY; SEQ ID NO:14), and/or γ$_{364-395}$ (DNGIIWATWKTRWYSMKKTTMKIIPFNRLTIG; SEQ NO:15) peptidyl epitopes as well. Antibodies directed against any of the SEQ ID NO:12-16 peptides can also effectively decrease inflammation in a mouse model of Covid-19 induced coagulopathy.

A sequence for a mouse fibrinogen (NCBI accession number NP_001304034.1) is shown below as SEQ ID NO:17.

```
  1 MSWSLQPPSF LLCCLLLLFS PTGLAYVATR DNCCILDERF

41 GSFCPTTCGI ADFLSSYQTD VDNDLRTLED ILFRAENRTT

81 EAKELIKAIQ VYYNPDQPPK PGMIDSATQK SKKMVEEIVK

121 YEALLLTHET SIRYLQEIYN SNNQKITNLK QKVAQLEAQC

161 QEPCKDSVQI HDTTGKDCQE IANKGAKESG LYFIRPLKAK

201 QQFLVYCEID GSGNGWTVLQ KRIDGSLDFK KNWIQYKEGF

241 GHLSPTGTTE FWLGNEKIHL ISMQSTIPYA LRIQLKDWNG

281 RTSTADYAMF RVGPESDKYR LTYAYFIGGD AGDAFDGYDF

321 GDDPSDKFFT SHNGMQFSTW DNDNDKFEGN CAEQDGSGWW

361 MNKCHAGHLN GVYHQGGTYS KSSTTNGFDD GIIWATWKSR

401 WYSMKETTMK IIPFNRLSIG EGQQHHMGGS KQVSVDHEVE

441 IEY
```

Note that this mouse fibrinogen has as a slightly different sequence in the region of the human fibrin epitope with any of the SEQ ID NO:12-15 sequences. Other mouse fibrinogen sequences also have sequences that differ from the human fibrinogen sequence in the region of any of the SEQ ID NO:12-15 sequences. The fact that antibodies directed against the human SEQ ID NO:12 epitope indicates that some variation in fibrinogen sequences does not adversely affect the efficacy for decreasing inflammation by anti-fibrinogen antibodies directed against the SEQ ID NO:12 epitope.

Antibodies

Anti-fibrin and/or anti-Spike protein antibodies can be tested to identify useful therapeutic agents for reducing the symptoms associated with SARS-CoV-2 infection and for inhibiting binding of SARS-CoV-2 to fibrin or fibrinogen.

Antibodies can be raised against various epitopes of the fibrinogen or fibrin or against various epitopes of a SARS-CoV-2 spike protein. Such antibodies can be used as test agents to ascertain their effectiveness for reducing the symptoms associated with SARS-CoV-2 infection and/or for inhibiting binding of SARS-CoV-2 to fibrin or fibrinogen. Some antibodies to be tested may be available commercially. However, the antibodies contemplated for treatment pursuant to the methods and compositions described herein are preferably human or humanized antibodies. The antibodies are also highly specific for their fibrinogen/fibrin or spike protein targets.

Fibrinogen peptide γ$_{377-395}$ is the binding site for the CD11b I-domain of complement receptor 3 (CR3) (also known as CD11b/CD18, Mac-1, α$_M$β$_2$) and is required for fibrin-induced activation of microglia and macrophages. A sequence for the CD11b/CD18 (Mac-1) protein is available as accession number P11215-1 from the Uniprot database and shown below as SEQ ID NO:18.

```
         10         20         30         40
MALRVLLLTA LTLCHGFNLD TENAMTFQEN ARGFGQSVVQ 50         60         70         80
LQGSRVVVGA PQEIVAANQR GSLYQCDYST GSCEPIRLQV 90        100        110        120
PVEAVNMSLG LSLAATTSPP QLLACGPTVH QTCSENTYVK 130        140        150        160
GLCFLFGSNL RQQPQKFPEA LRGCPQEDSD IAFLIDGSGS 170        180        190        200
IIPHDFRRMK EFVSTVMEQL KKSKTLFSLM QYSEEFRIHF 210        220        230        240
TFKEFQNNPN PRSLVKPITQ LLGRTHTATG IRKVVRELFN 250        260        270        280
ITNGARKNAF KILVVITDGE KFGDPLGYED VIPEADREGV 290        300        310        320
IRYVIGVGDA FRSEKSRQEL NTIASKPPRD HVFQVNNFEA 330        340        350        360
LKTIQNQLRE KIFAIEGTQT GSSSSFEHEM SQEGFSAAIT 370        380        390        400
SNGPLLSTVG SYDWAGGVFL YTSKEKSTFI NMTRVDSDMN 410        420        430        440
DAYLGYAAAI ILRNRVQSLV LGAPRYQHIG LVAMFRQNTG 450        460        470        480
MWESNANVKG TQIGAYFGAS LCSVDVDSNG STDLVLIGAP 490        500        510        520
HYYEQTRGGQ VSVCPLPRGR ARWQCDAVLY GEQGQPWGRF 530        540        550        560
GAALTVLGDV NGDKLTDVAI GAPGEEDNRG AVYLFHGTSG 570        580        590        600
SGISPSHSQR IAGSKLSPRL QYFGQSLSGG QDLTMDGLVD 610        620        630        640
LTVGAQGHVL LLRSQPVLRV KAIMEFNPRE VARNVFECND 650        660        670        680
QVVKGKEAGE VRVCLHVQKS TRDRLREGQI QSVVTYDLAL 690        700        710        720
DSGRPHSRAV FNETKNSTRR QTQVLGLTQT CETLKLQLPN 730        740        750        760
CIEDPVSPIV LRLNFSLVGT PLSAFGNLRP VLAEDAQRLF 770        780        790        800
TALFPFEKNC GNDNICQDDL SITFSFMSLD CLVVGGPREF
```

-continued

```
       810         820         830         840
NVTVTVRNDG  EDSYRTQVTF  FFPLDLSYRK  VSTLQNQRSQ 850         860         870         880
RSWRLACESA  SSTEVSGALK  STSCSINHPI  FPENSEVTFN 890         900         910         920
ITFDVDSKAS  LGNKLLLKAN  VTSENNMPRT  NKTEFQLELP 930         940         950         960
VKYAVYMVVT  SHGVSTKYLN  FTASENTSRV  MQHQYQVSNL 970         980         990        1000
GQRSLPISLV  FLVPVRLNQT  VIWDRPQVTF  SENLSSTCHT 1010        1020        1030        1040
KERLPSHSDF  LAELRKAPVV  NCSIAVCQRI  QCDIPFFGIQ 1050        1060        1070        1080
EEFNATLKGN  LSFDWYIKTS  HNHLLIVSTA  EILFNDSVFT 1090        1100        1110        1120
LLPGQGAFVR  SQTETKVEPF  EVPNPLPLIV  GSSVGGLLLL 1130        1140        1150
ALITAALYKL  GFFKRQYKDM  MSEGGPPGAE  PG
```

Desirable the anti-fibrin/anti-fibrinogen antibodies can block the binding of Mac-1 (CD11b/CD18) to fibrin or fibrinogen. Such antibodies can, for example, block SARS-CoV-2-related inflammation by disrupting the fibrin/Mac-1 interaction. The data disclosed herein demonstrates that such anti-fibrin antibodies do in fact reduce inflammation in SARS-CoV-2-infected animals.

The inventors have determined that the SARS-CoV-2 Spike protein can bind to fibrin and that anti-fibrin anti-fibrinogen antibodies can inhibit binding of the SARS-CoV-2 Spike protein to fibrin. Binding of SARS-CoV-2 via its Spike protein to fibrin can trigger inflammation.

The antibodies tested may be monoclonal antibodies. Such antibodies may also be humanized or fully human monoclonal antibodies. The antibodies can exhibit one or more desirable functional properties, such as high affinity binding to fibrinogen or fibrin, or the ability to inhibit binding of fibrinogen or fibrin to the SARS-CoV-2 Spike protein.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $CH_3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g. a peptide or domain of fibrinogen, fibrin, or the SARS-CoV-2 spike protein).

The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds fibrinogen/fibrin or a SARS-CoV-2 spike protein, is substantially free of antibodies that specifically bind antigens other than fibrinogen/fibrin or the SARS-CoV-2 spike protein. An isolated antibody that specifically binds fibrinogen/fibrin or a SARS-CoV-2 spike protein may, however, have cross-reactivity to other antigens, such as isoforms, mutant or related fibrinogen/fibrin or a SARS-CoV-2 spike proteins from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_L$, and $V_H$ regions of the recombinant antibodies are sequences that, while derived from and related to human germline $V_L$ and $V_H$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human fibrinogen/fibrin or a SARS-CoV-2 spike protein" is intended to refer to an antibody that binds to human fibrinogen/fibrin or a SARS-CoV-2 spike protein with a $K_D$ of $1 \times 10^{-7}$M or less, more preferably $5 \times 10^{-8}$ M or less, more preferably $1 \times 10^{-8}$ M or less, more preferably $5 \times 10^{-9}$ M or less, even more preferably between $1 \times 10^{-8}$ M and $1-10^{-10}$ M or less.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The antibodies of the invention are characterized by particular functional features or properties of the antibodies. For example, the antibodies bind specifically to human fibrinogen/fibrin or a SARS-CoV-2 spike protein. Preferably, an antibody deemed to be useful can bind to fibrinogen/fibrin or a SARS-CoV-2 spike protein with high affinity, for example with a $K_D$ of $1 \times 10^{-7}$ M or less. Useful antibodies can exhibit one or more of the following characteristics:

(a) binds to human fibrinogen or fibrin with a $K_D$ of $1 \times 10^{-7}$ M or less;

(b) binds to SARS-CoV-2 spike protein with a $K_D$ of $1 \times 10^{-7}$ M or less;

(b) inhibits the binding of fibrinogen or fibrin to the SARS-CoV-2 Spike protein;

(c) inhibits SARS-CoV-2-related inflammation; or (d) a combination thereof.

For example, the antibodies identified as useful by the methods described herein can prevent greater than 30% binding, or greater than 40% binding, or greater than 50% binding, or greater than 60% binding, or greater than 70% binding, or greater than 80% binding, or greater than 90% binding of SARS-CoV-2 or Mac-1 to fibrinogen/fibrin.

Assays to evaluate the binding ability of the antibodies to fibrinogen/fibrin or the SARS-CoV-2 spike protein can be used, including for example, ELISAs, Western blots and RIAs. The binding kinetics (e.g., binding affinity) of the antibodies also can be assessed by standard assays known in the art, such as by Biacore™. analysis.

Given that each of the subject antibodies can bind to fibrinogen/fibrin or the SARS-CoV-2 spike protein, the $V_L$ and $V_H$ sequences can be "mixed and matched" to create other binding molecules that bind to fibrinogen/fibrin or the SARS-CoV-2 spike protein. The binding properties of such "mixed and matched" antibodies can be tested using the binding assays described above and assessed in assays described in the examples. When $V_L$ and $V_H$ chains are mixed and matched, a $V_H$ sequence from a particular $V_H/V_L$ pairing can be replaced with a structurally similar $V_H$ sequence. Likewise, preferably a $V_L$ sequence from a particular $V_H/V_L$ pairing is replaced with a structurally similar $V_L$ sequence.

Accordingly, useful agents identified by the methods described herein can be isolated monoclonal antibodies, or antigen binding portions thereof comprising:

(a) a heavy chain variable region comprising an amino acid sequence; and (b) a light chain variable region comprising an amino acid sequence;

wherein the antibody specifically binds fibrinogen/fibrin or the SARS-CoV-2 spike protein.

In some cases, the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., British J. of Cancer 83(2):252-260 (2000) (describing the production of a humanized anti-CD30 antibody using only the heavy chain variable domain CDR3 of murine anti-CD30 antibody Ki-4); Beiboer et al., J. Mol. Biol. 296:833-849 (2000) (describing recombinant epithelial glycoprotein-2 (EGP-2) antibodies using only the heavy chain CDR3 sequence of the parental murine MOC-31 anti-EGP-2 antibody); Rader et al., Proc. Natl. Acad. Sci. U.S.A. 95:8910-8915 (1998) (describing a panel of humanized anti-integrin alpha$_v$beta$_3$ antibodies using a heavy and light chain variable CDR3 domain. Hence, in some cases a mixed and matched antibody or a humanized antibody contains a CDR3 antigen binding domain that is specific for fibrinogen/fibrin or the SARS-CoV-2 spike protein.

Monoclonal antibodies generated can inhibit fibrinogen-SARS-CoV-2 binding. For example, the methods described herein can in some cases be monoclonal antibodies that specifically bind the $\gamma^{377\text{-}395}$ epitope of the fibrin and fibrinogen γC domain or to a SARS-CoV-2 spike protein epitope. Such antibodies can block the damaging effects of SARS-CoV-2 relating to inflammation. Such monoclonal antibodies can inhibit binding of fibrin and fibrinogen to the SARS-CoV-2 Spike protein.

One example of an antibody with excellent fibrin binding properties is the 5B8 monoclonal antibody. Various polynucleotide and polypeptide sequences related to the 5B8 antibody are described hereinbelow. These sequences include the 5B8 light chain amino acid sequence (SEQ ID NO:19), shown below.

```
  1 TFDSPYQVRR MRFSAQLLGL LVLWIPGSTA DIVMTQAAFS

41 NPITLGTSAS MSCRSSKSLL HSSGITYLSW YLQKPGQSPQ

81 LLIYQMSNLA SGVPDRFSSS GSGTDFTLRI SRVEAEDVGV

121 YYCAQNLELP LTFGAGTKLE LKRADAAPTV SACTKGEF
```

Three 5B8 antibody light chain CDR amino acid sequences (CDR-L1, CDR-L2, and CDR-L3), are shown below as SEQ ID NO:20, 21, and 22, respectively.

The CDR-L1 sequence (SEQ NO:20) is RSSKSLLHSSGITYLS.

The CDR-L2 sequence (SEQ ID NO:21) is QMSNLAS.

The CDR-L3 sequence (SEQ ID NO:22) is AQNLELPLT.

Three 5B8 antibody heavy chain amino acid sequence is shown below as (SEQ ID NO:23).

```
  1 NTAFAGFGRN MRSLFSLQLL STQDLAMGWS CIIVLLVSTA

41 TGVHSQVQLQ QPGAELVRPG TSVKLSCKAS GYTFTSYWIH

81 WVKQRPGQGL EWIGLIDPSD SYTNYNQKFR GKATLTVDTS

121 SSTAYMQLSS LTSEDSAVYY CASSDPTGCW GQGTTLTVSP

161 ASTTPP
```

Three heavy chain CDR amino acid sequences (CDR-H1, CDR-H2, and CDR-H3), are shown below as SEQ ID NO:24, 25, and 26, respectively.

The CDR-H1 sequence (SEQ ID NO:24) is GYTFTSYWIH.

The CDR-H2 sequence (SEQ ID NO:25) is LIDPSDSYTNYNQKFR.

The CDR-H3 sequence (SEQ ID NO:26) is SDPTGC.

The 5B8 antibody light chain nucleotide sequence is shown below as SEQ ID NO:27.

```
  1 ACTTTTGACT CACCATATCA AGTTCGCAGA ATGAGGTTCT

41 CTGCTCAGCT TCTGGGGCTG CTTGTGCTCT GGATCCCTGG

81 ATCCACTGCA GATATTGTGA TGACGCAGGC TGCATTCTCC

121 AATCCAATCA CTCTTGGAAC ATCAGCTTCC ATGTCCTGCA

161 GGTCTAGTAA GAGTCTCCTA CATAGTAGTG GCATCACTTA

201 TTTGTCTTGG TATCTGCAGA AGCCAGGCCA GTCTCCTCAG

241 CTCCTGATTT ATCAGATGTC CAACCTTGCC TCAGGAGTCC

281 CAGACAGGTT CAGTAGCAGT GGGTCAGGAA CTGATTTCAC

321 ACTGAGAATT AGCCGAGTGG AGGCTGAGGA TGTGGGTGTT

361 TATTACTGTG CTCAAAATCT AGAACTTCCG CTCACGTTCG

401 GTGCTGGGAC CAAGCTGGAG CTGAAACGGG CTGATGCTGC

441 ACCAACTGTA TCCGCATGCA CCAAGGGCGA ATTC
```

The 5B8 antibody heavy chain nucleotide sequence is shown below as SEQ ID NO:28.

```
  1 GAACACTGCG TTTGCTGGCT TTGGAAGAAA CATGAGATCA

41 CTGTTCTCTC TACAGTTACT GAGCACACAG GACCTCGCCA

81 TGGGATGGAG CTGTATCATT GTCCTCTTGG TATCAACAGC

121 TACAGGTGTC CACTCCCAGG TCCAACTGCA GCAGCCTGGG

161 GCTGAGCTGG TGAGGCCTGG GACTTCAGTG AAGTTGTCCT

201 GCAAGGCTTC TGGCTACACC TTCACCAGCT ACTGGATACA

241 CTGGGTAAAG CAGAGGCCTG GACAAGGCCT TGAGTGGATC

281 GGACTGATTG ATCCTTCTGA TAGTTATACT AACTACAATC

321 AAAAGTTCAG GGGCAAGGCC ACATTGACTG TAGACACATC

361 CTCCAGCACA GCCTACATGC AGCTCAGCAG CCTGACATCT

401 GAGGACTCTG CGGTCTATTA CTGTGCAAGC TCCGATCCTA

441 CAGGCTGCTG GGGCCAAGGC ACCACTCTCA CAGTCTCCCC

481 AGCTAGCACA ACACCCCCA
```

Nucleotide sequences of the three 5B8 antibody light chain CDRs (CDR-L1, CDR-L2, and CDR-L3), are shown below as SEQ ID NO:29, 30, and 31, respectively.

The 5B8 antibody light chain CDR-L1 nucleotide sequence is: AGGTCTAGTA AGAGTCTCCT ACATAGTAGT GGCATCACTT ATTTGTCT (SEQ ID NO:29).

The 5B8 antibody light chain CDR-L2 nucleotide sequence is: CAGATGTCCA ACCTTGCCTC (SEQ NO:30).

The 5B8 antibody light chain CDR-L3 nucleotide sequence is: GCTCAAAATC TAGAACTTCC GCTCACG (SEQ ID NO:31).

Nucleotide sequences of the three 5B8 antibody heavy chain CDRs (CDR-H1, CDR-H2, and CDR-H3), are shown below as SEQ ID NO:32, 33, and 34, respectively.

The 5B8 antibody heavy chain CDR-H1 nucleotide sequence is: GGCTACACCT TCACCACGCTA CTGGATACAC (SEQ ID NO:32).

The 5B8 antibody heavy chain CDR-H2 nucleotide sequence is: CTGATTGATC CTTCTGATAG TTATACTAAC TACAATCAAA AGTTCAGGGG C (SEQ ID NO: 33).

The 5B8 antibody heavy chain CDR-H3 nucleotide sequence is: TCCGATCCTA CAGGCTGC (SEQ ID NO:34).

The sequences provided herein, including the fibrin, fibrinogen, epitope and antibody sequences, are exemplary. Isoforms and variants of these sequences can also be used in the methods and compositions described herein.

For example, isoforms and variants of the amino acid and nucleic acids described herein can be used in the methods and compositions described herein so long as they are substantially identical to the fibrin, spike protein, and antibody sequences described herein. The terms "substantially identity" indicates that a polypeptide or nucleic acid has a sequence with between 55-100% sequence identity to a reference sequence, for example with at least 55% sequence identity, preferably 60%, preferably 70%, preferably 80%, preferably at least 90%, preferably at least 95%, preferably at least 96%, preferably at least 97% sequence, preferably at least 98%, preferably at least 99% identity to a reference sequence over a specified comparison window. Optimal alignment may be ascertained or conducted using the homology alignment algorithm of Needleman and Wunsch, J. Mol. Biol. 48:443-53 (1970).

An indication that two antibody or two polypeptide sequences are substantially identical is that both antibodies or both polypeptides have the same function, for example fibrin binding of the SARS-CoV-2 Spike protein or blocking inflammation in the lungs. The antibodies that are substantially identical to a 5B8 antibody sequence may not have exactly the same level of activity as the 5B8 antibody. Instead, the substantially identical antibody may exhibit greater or lesser levels of binding affinity to fibrin or to the SARS-CoV-2 Spike protein. For example, the substantially identical antibody or nucleic acid encoding the antibody may have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%. or at least about 140%, or at least about 150%, or at least about 200% of the binding affinity of the 5B8 antibody described herein when measured by similar assay procedures.

Compositions

The useful active agents identified in the test agent screens described herein can be formulated into compositions containing those active agents. Such active agents can antibodies, nucleic acids encoding antibodies (e.g., within an expression cassette or expression vector), polypeptides, small molecules, or a combination thereof. The compositions can be pharmaceutical compositions. In some embodiments, the compositions can include a pharmaceutically acceptable carrier. By "pharmaceutically acceptable" it is meant that a carrier, diluent, excipient, and/or salt is compatible with the other ingredients of the formulation, and not deleterious to the recipient thereof.

The composition can be formulated in any convenient form. In some embodiments, the compositions can include antibody, polypeptide, or small molecule that can inhibit binding of fibrinogen/fibrin to SARS-CoV-2 virions or to a SARS-CoV-2 Spike protein. In some embodiments, the compositions can include at least one antibody, polypeptide, or a small molecule that can bind to a SARS-CoV-2 Spike protein. In some embodiments, the compositions can include at least one antibody, polypeptide, or a small molecule that can bind to at least one SEQ ID NO:12-15 epitope. In other embodiments, the compositions can include at least one nucleic acid or expression cassette encoding an antibody or polypeptide that can bind to at least one SEQ ID NO:12-15 epitope or a SARS-CoV-2 Spike epitope.

In some embodiments, the active agents of the invention (e.g., antibodies, nucleic acids encoding an antibody (e.g., within an expression cassette or expression vector), polypeptides, small molecules, or a combination thereof), are administered in a "therapeutically effective amount." Such a therapeutically effective amount is an amount sufficient to obtain the desired physiological effect, such reduction of at least one symptom of SARS-CoV-2 infection. For example, active agents can reduce the symptoms of COVID-19 infection such as inflammation, oxidative stress, fibrin deposition, clot formation, blood brain barrier deterioration, fatigue, shortness of breath, cough, joint pain, chest pain, or combinations thereof, by 5%, or 10%, or 15%, or 20%, or 25%, or 30%, or 35%, or 40%, or 45%, or 50%, or 55%, or 60%, or 65%, or %70, or 80%, or 90%, 095%, or 97%, or 99%, or any numerical percentage between 5% and 100%.

To achieve the desired effect(s) the active agents may be administered as single or divided dosages. For example, active agents can be administered in dosages of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the type of antibodies, polypeptides, small molecules, or nucleic acid chosen for administration, the severity of the condition, the weight, the physical condition, the health, and the age of the mammal. Such factors can be readily determined by the clinician employing animal models or other test systems that are available in the art.

Administration of the active agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the active agents and compositions of the invention may be essentially continuous over a preselected period of time or may be in a series of spaced doses. Both local and systemic administration is contemplated.

To prepare the antibodies, polypeptides, small molecules, nucleic acids, expression cassettes, and other agents are synthesized or otherwise obtained, purified as necessary or desired. These antibodies, polypeptides, small molecules, nucleic acids, expression cassettes, and other agents can be suspended in a pharmaceutically acceptable carrier and/or lyophilized or otherwise stabilized. The antibodies, polypeptides, small molecules, nucleic acids, expression cassettes, other agents, and combinations thereof can be adjusted to an appropriate concentration, and optionally combined with other desired agents. The absolute weight of a given antibody, polypeptide, small molecule nucleic acid, expression vector, and/or another agent included in a unit dose can vary widely. For example, about 0.01 to about 2 g, or about 0.1 to about 500 mg, of at least one antibody, nucleic acid, polypeptide, small molecule, expression cassette, and/or other agent, or a plurality of antibodies, nucleic acids, polypeptides, small molecules, expression cassettes, and/or other agents can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 grams anti-Fibrin(ogen) 5B8 antibodies (30 mg/kg).

Daily doses of the agents of the invention can vary as well. Such daily doses can range, for example, from about 0.001 g/day to about 50 g/day, from about 0.01 g/day to about 2.5 g/day, from about 0.01 g/day to about 12 g/day, from about 0.5 g/day to about 8 g/day, from about 0.5 g/day to about 4 g/day, and from about 0.5 g/day to about 2 g/day.

It will be appreciated that the amount of the agent for use in treatment will vary not only with the particular carrier selected but also with the route of administration, the severity of the condition being treated and the age and condition of the patient. Ultimately the attendant health care provider can determine proper dosage. In addition, a. pharmaceutical composition can be formulated as a single unit dosage form.

Thus, one or more suitable unit dosage forms comprising the agent(s) can be administered by a variety of routes including parenteral (including subcutaneous, intravenous, intramuscular and intraperitoneal), oral, rectal, dermal, transdermal, intrathoracic, intrapulmonary and intranasal (respiratory) routes. The agent(s) may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the agents with liquid carriers, solid matrices, semi-solid carriers, finely divided solid carriers or combinations thereof, and then, if necessary, introducing or shaping the product into the desired delivery system. For example, the agents) can be linked to a convenient carrier such as a nanoparticle, albumin, polyalkylene glycol, or be supplied in prodrug form. The agent(s) and combinations thereof, can be combined with a carrier and/or encapsulated in a vesicle such as a liposome.

The compositions of the invention may be prepared in many forms that include aqueous solutions, suspensions, tablets, hard or soft gelatin capsules, and liposomes and other slow-release formulations, such as shaped polymeric gels. Administration of active agents can also involve parenteral or local administration of the in an aqueous solution or sustained release vehicle.

Thus, while the agents can sometimes be administered in an oral dosage form, that oral dosage form can be formulated so as to protect the antibodies, polypeptides, small molecules, nucleic acids, expression cassettes, and combinations thereof from degradation or breakdown before the antibodies, polypeptides, small molecules, nucleic acids encoding such polypeptides/antibodies, and combinations thereof provide therapeutic utility. For example, in some cases the antibodies, polypeptides, small molecules, nucleic acids encoding such antibodies/polypeptides, and/or other agents can be formulated for release into the intestine after passing through the stomach. Such formulations are described, for example, in U.S. Pat. No. 6,306,434 and in the references contained therein.

Liquid pharmaceutical compositions may be in the form of, for example, aqueous or oily suspensions, solutions, emulsions, syrups or elixirs, dry powders for constitution with water or other suitable vehicle before use. Such liquid pharmaceutical compositions may contain conventional additives such as suspending agents, emulsifying agents, non-aqueous vehicles (which may include edible oils), or preservatives. The pharmaceutical compositions may take such forms as suspensions, solutions, or emulsions in oily or aqueous vehicles, and may contain formulator/agents such as suspending, stabilizing and/or dispersing agents. Suitable carriers include saline solution, encapsulating agents (e.g., liposomes), and other materials. The agents can be formulated in dry form (e.g., in freeze-dried form), in the presence or absence of a carrier. If a carrier is desired, the carrier can be included in the pharmaceutical formulation, or can be separately packaged in a separate container, for addition to the agents, after packaging in dry form, in suspension, or in soluble concentrated form in a convenient liquid.

Active agent(s) and/or other agents can be formulated for parenteral administration (e.g., by injection, for example, bolus injection or continuous infusion) and may be presented in unit dosage form in ampoules, prefilled syringes, small volume infusion containers or multi-dose containers with an added preservative.

The compositions can also contain other ingredients such as anti-viral agents, antibacterial agents, antimicrobial agents, immune modulators, other monoclonal antibodies, and/or preservatives.

The present description is further illustrated by the following examples, which should not be construed as limiting in any way. The contents of all cited references (including literature references, issued patents, published patent applications as cited throughout this application) are hereby expressly incorporated by reference.

Example 1: Animal Model of SARS-CoV-2 Adverse Symptoms This Example illustrates how to make the Animal Model of SARS-CoV-2 symptoms.

Pseudotyped SARS-CoV-2 that express the wild type Spike were generated by using an HIV-delta Env packaging vector (HIV proviral DNA lacking its natural Env gene; HIV-1 NL4-3 ΔEnv EGFP Reporter Vector) with a viral packaging system (see FIG. 1A). The HIV-1 NL4-3 ΔEnv EGFP vector does not express the HIV Envelope protein (see hivreagentprogram.org catalog no. ARP-11100). An example of a sequence for a plasmid/expression vector for SARS-CoV-2 Spike protein is the pCAGGS vector with the NR-52310 Spike protein insert provided by beiresources.org. 'BALD' virions that do not express the SARS-CoV-2 Spike protein or the HIV Env protein were generated to serve as a negative control.

For production of HIV-1 NL-43ΔEnv-eGFP SARS CoV-2 Spike pseudotyped virus particles, 293T cells were plated at $3.75 \times 10^6$ cells in a T175 flask. Twenty four hours post plating the cells were transfected by PEI transfection reagent (Sigma) with 90 ug of PEI, 30 ug of HIV-1 NL-4 Δ Env eGFP (NIH AIDS Reagent Program) and 3.5 ug of pCAGGS SARS CoV-2 Spike Glycoprotein (NR52310, BEI) in a total of 10 mL of Opti-MEM™ media (Invitrogen). The day following transfection the media was changed to DMEM10 complete media and placed at 37° C. and 5% $CO_2$ for 48 hours. At 48 hours, the supernatant was harvested, filtered by 0.22 μm Steriflip© filters (EMD, Millipore) and then concentrated by ultracentrifugation for 1.5 hours at 4° C. and 25K rpm. After concentration, the supernatant was removed and virus particle pellets were resuspended in cold 1×PBS containing 1% FBS, aliquots were stored at −80° c. For production of control virus particles not expressing the SARS CoV-2 Spike glycoprotein (Bald), the same procedure was used but with the omission of the pCAGGS SARS CoV-2 Spike vector transfection. SARS and MERS pseudotyped virus particles were produced using the same procedure, substituting the SARS CoV-2 spike expression vector with either pcDNA3.1(+) SARS spike or pcDNA3.1(+) MERS spike.

Figure 1B:
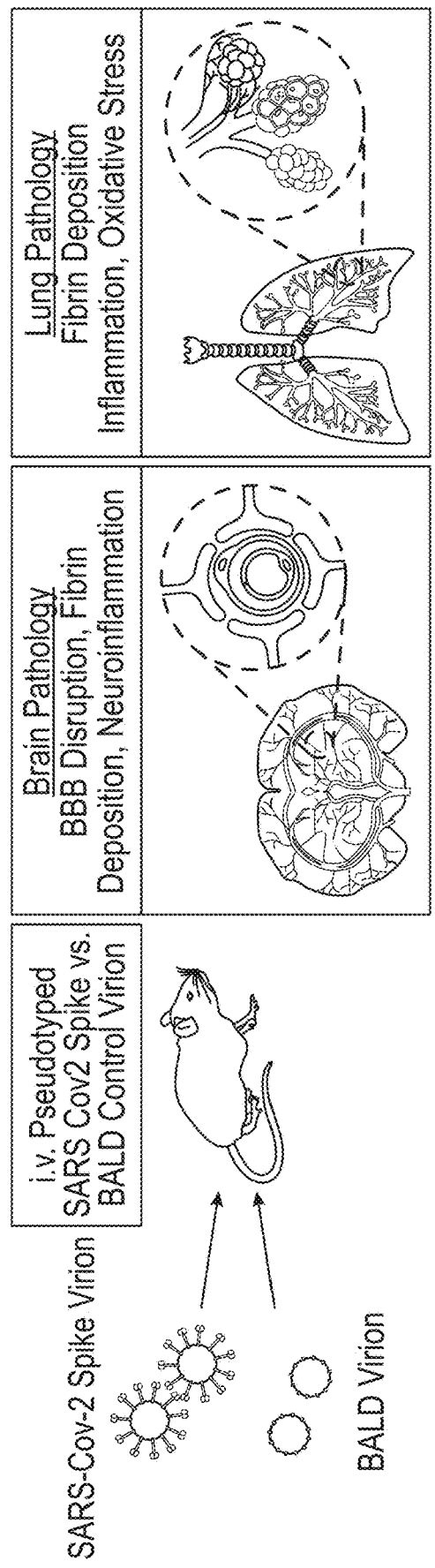

Mice were selected as an animal model for evaluation of the effects of SARS-CoV-2 infection on various organ systems and the procedure illustrated in FIG. 1B illustrates administration of the pseudotyped Spike and BALD SARS-CoV-2 viral particles to the mice and the pathological effects on the animals were monitored.

Pseudotyped SARS-CoV-2 Spike protein virion administration negatively affected the brain and the lungs of the mice. In the brain, neuroinflammation was prevalent, the blood brain barrier was disrupted, and fibrin deposition was visible. The lungs also exhibited inflammation and fibrin deposition, as well as oxidative stress. See FIGS. 2-5.

Figure 2A:
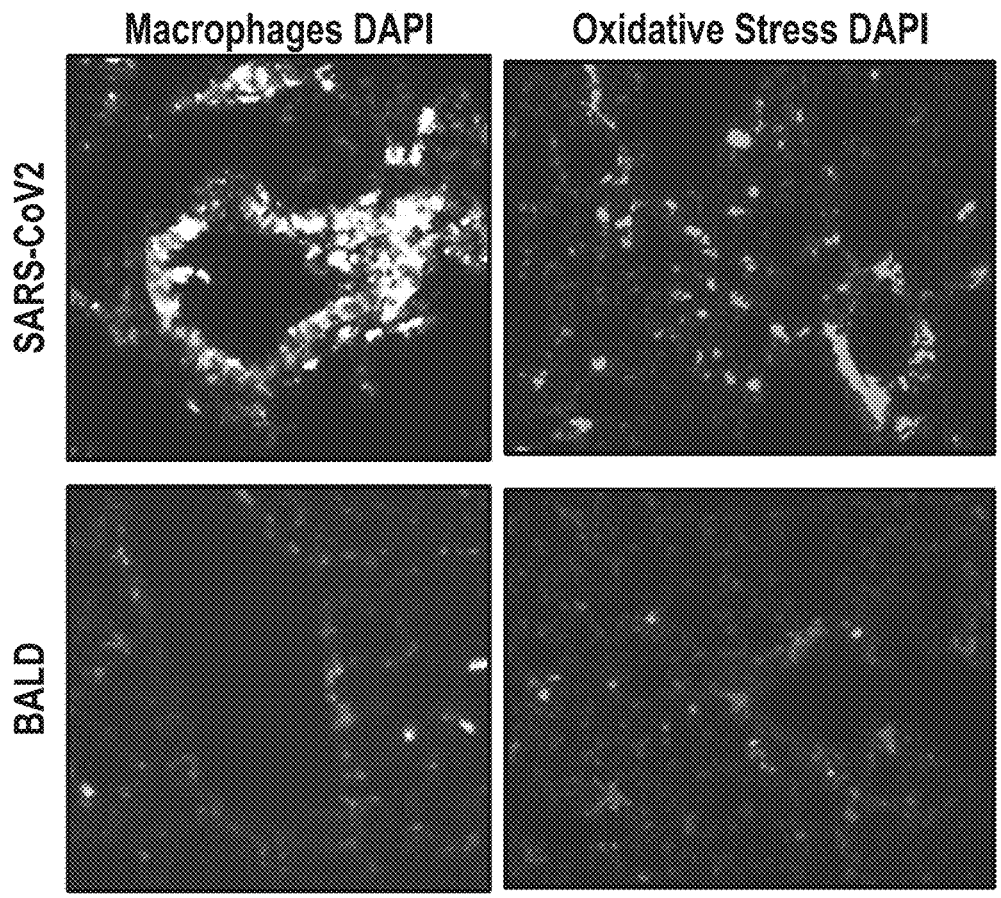
FIG. 2A-2C illustrate that, like the effects of SARS-CoV-2 on humans, SARS-CoV-2-exhibits macrophage infiltration, oxidative stress, and inflammation in the lungs of mice infected with SARS-CoV-2.
Figure 2B:
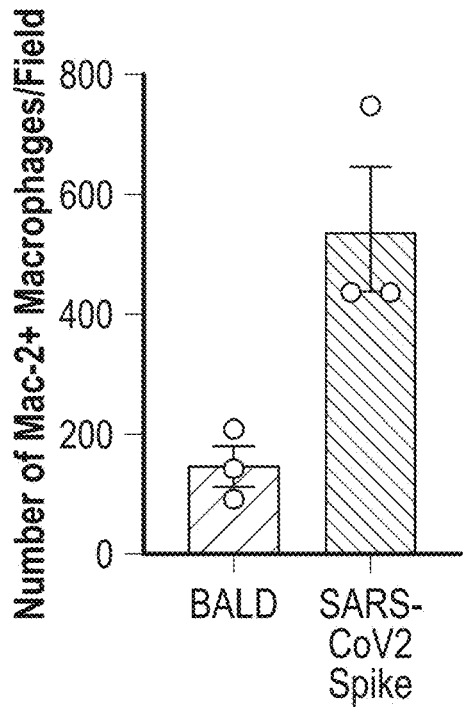
Figure 2C:
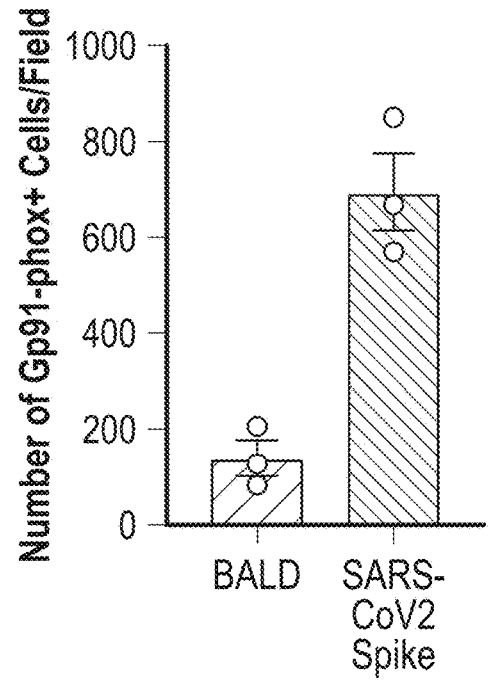

FIG. 2A-2C illustrate that, like the effects of SARS-CoV-2 on humans, SARS-CoV-2 induces macrophage infiltration, oxidative stress, and inflammation in the lungs of the mouse animal model infected with SARS-CoV-2. FIG. 2A shows images of lung sections from mice infected with SARS-CoV-2 (top two panels) and with non-infective, 'bald' SARS-CoV-2 virions particles with no spike proteins. The two left panels were stained with a labeled anti-Mac-2 antibody to detect macrophages, while the two right panels were stained with anti-Gp91-phox antibodies to detect oxidative stress. FIG. 2B graphically illustrates the number of macrophages per field in the lungs of mice infected with wild type SARS-CoV-2 and non-infective 'bald' SARS-CoV-2. FIG. 2C graphically illustrates the number Gp91-phox$^+$ cells per field, where expression of Gp91-phox is a marker for oxidative stress.

Figure 3A:
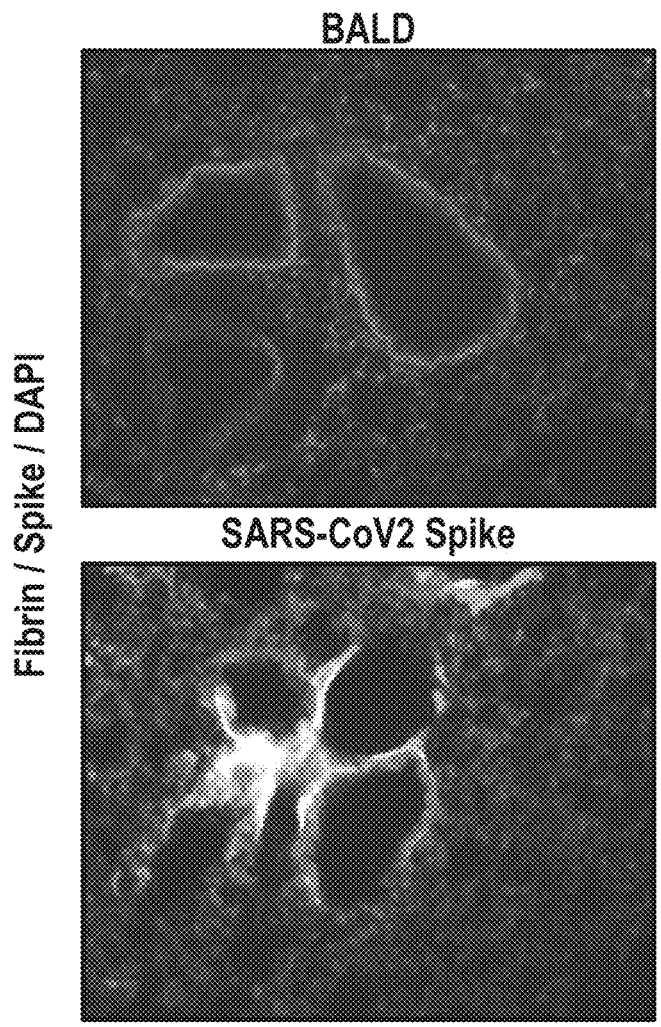
FIG. 3A-3B illustrate that fibrin and the SARS-CoV-2 Spike protein co-localize in the lungs of mice administered virions pseudotyped with SARS-CoV-2 Spike.
Figure 3B:
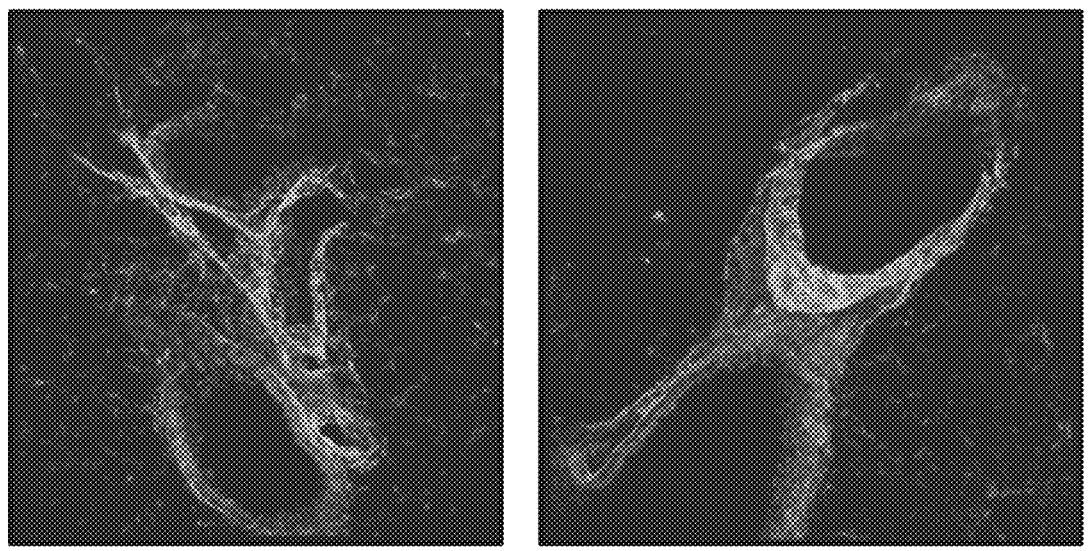

FIG. 3A-3B illustrate that fibrin and the SARS-CoV-2 spike protein co-localize in the lungs of mice infected with SARS-COV-2. FIG. 3A shows images of lung sections of mice infected with SARS-CoV-2 (bottom panel) and mice infected with non-infective, 'bald' SARS-COV-2 virions particles that have no spike proteins (top panel), where the lung sections were stained with labeled anti-fibrin and anti-spike antibodies. FIG. 3B shows higher magnification images of lung sections of mice infected with SARS-CoV-2 stained with labeled anti-fibrin and anti-spike antibodies.

Figures 4A, 4B:
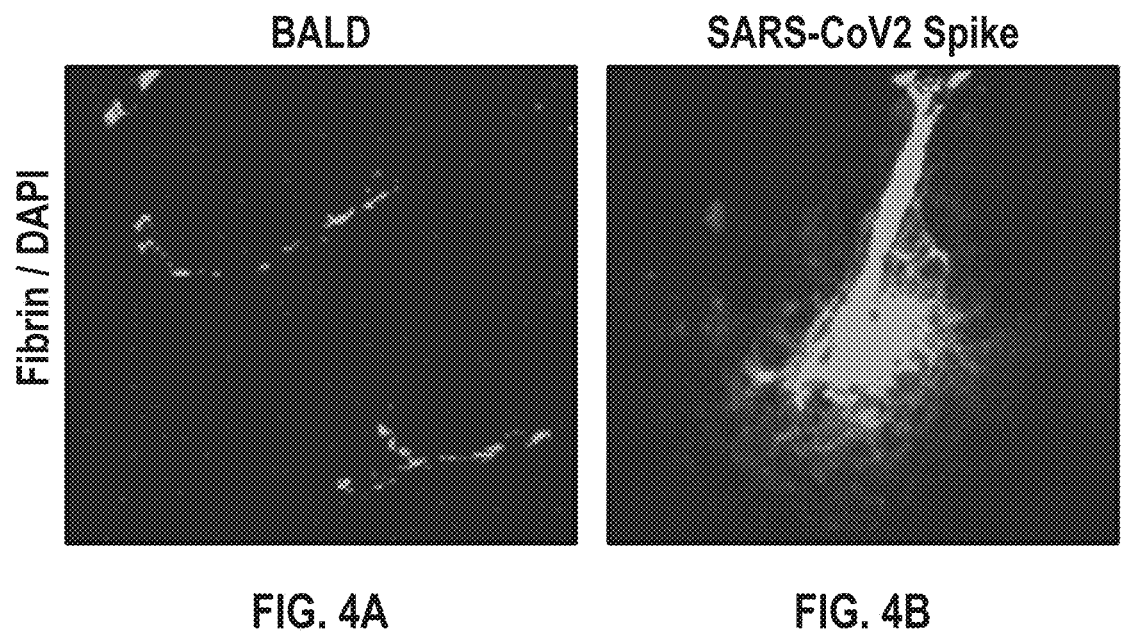
FIG. 4A-4B illustrate that exposure to pseudotyped virions containing SARS-CoV-2 Spike induces fibrin deposition in the brains of mice.

FIG. 4A-4B illustrates that SARS-CoV-2 infection induces fibrin deposition in the brains of mice. FIG. 4A is an image of a brain section from a mouse infected with non-infective, 'bald' SARS-CoV-2 virions particles that have no spike proteins infected with non-infective, 'bald' SARS-CoV-2 virions particles that have no spike proteins after staining with labeled anti-fibrin antibodies. FIG. 4B is an image of a brain section from a mouse infected with SARS-CoV-2 virions particles after staining with labeled anti-fibrin antibodies. However, Fibrin deposition had low penetrance. In contrast to the lung, which is very reproducible with 100% of the mice developing prominent pathology, the brain in the in the animal model had little pathology and was not observed in other animals.

Figures 5A, 5B:
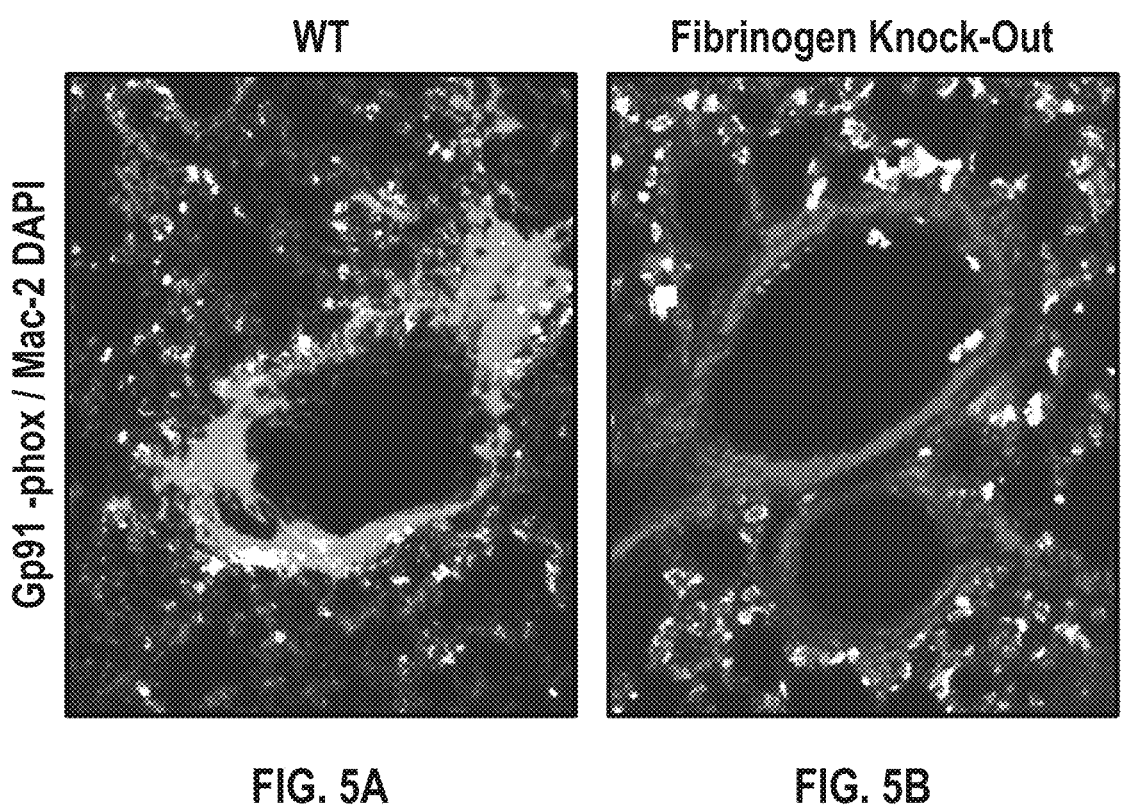
FIG. 5A-5B illustrates that fibrin expression is necessary for inflammation ensuing after infection with virions expressing SARS-CoV-2 Spike.

FIG. 5A-5B illustrates that fibrin expression is necessary for SARS-CoV-2-induced inflammation. FIG. 5A shows a lung section from a wild type mouse that had been infected with SARS-CoV-2 after staining with labeled anti-Mac-2 and anti-Gp91-phox antibodies to detect macrophage infiltration and oxidative stress, respectively. FIG. 5B shows a lung section from a fibrinogen gene knockout mouse after the section was stained with labeled anti-Mac-2 and anti-Gp91-phox antibodies to detect macrophage infiltration and oxidative stress.

Note that while the mice express ACE2 receptors, which is the receptor bound by SARS- CoV-2 the Spike protein in humans, the SARS-CoV-2 Spike protein does not bind to the mouse version of ACE2. It is surprising that pseudotyped virions that express only the SARS-CoV-2 Spike protein exhibit physiological effects in mice that are so similar to those observed in humans.

Example 2: SARS-CoV-2 Binds Fibrin and Promotes Clotting

The Example illustrates that the SARS-CoV-2 Spike protein binds fibrin and promotes clotting as detected in an in vitro assay.

Aliquots of pseudotyped SARS-CoV-2 Spike virions and pseudotyped 'bald' virions that do not express Spike proteins were separately incubated with human fibrinogen. A mixture of thrombin and calcium chloride was added to the SARS-CoV-2 Spike virion-fibrinogen and BALD virion-fibrinogen mixtures. Fibrin polymerization was quantified over time.

Figure 6:
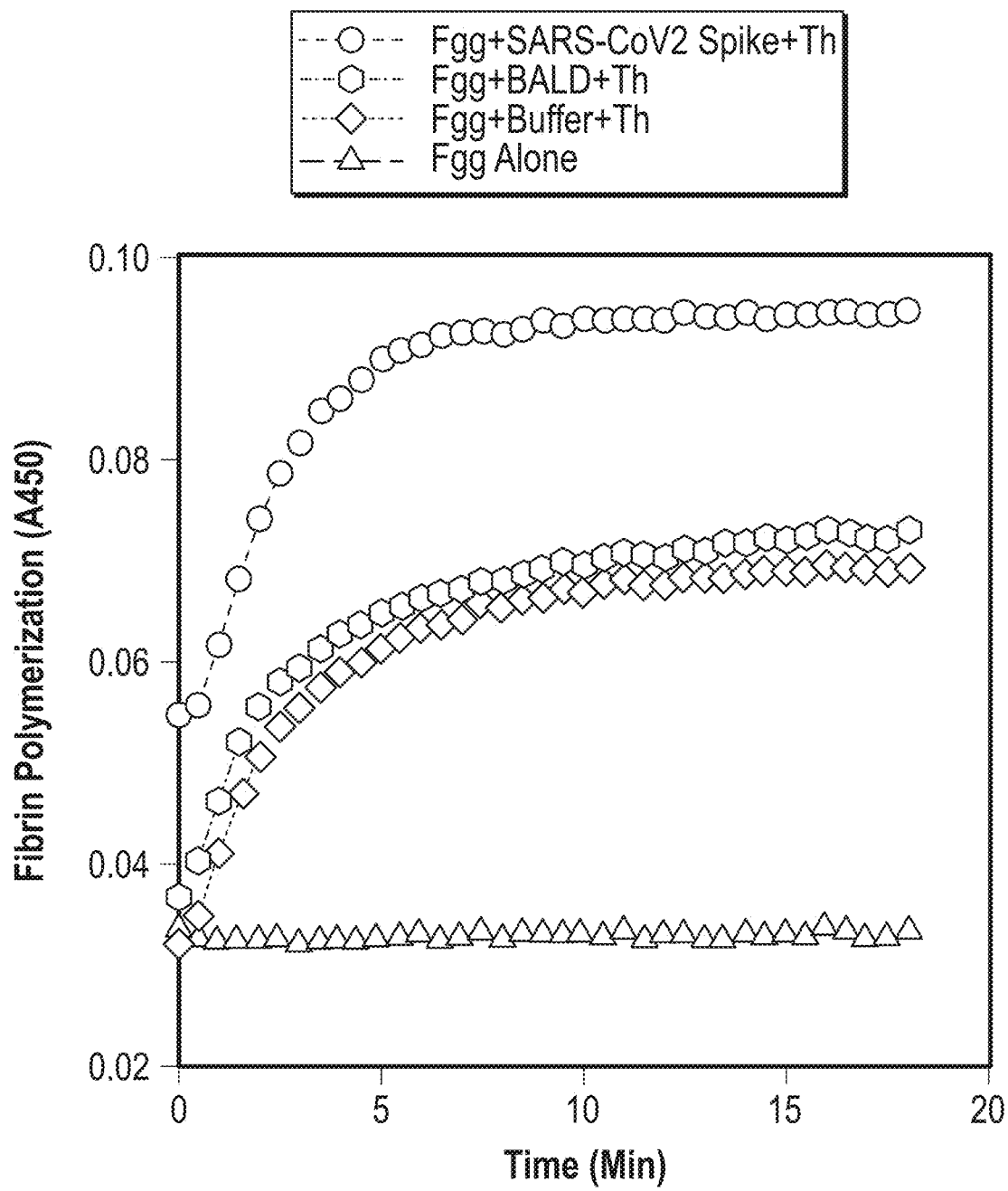
FIG. 6 graphically illustrates that SARS-CoV-2 Spike-pseudotyped virions bind fibrin and induce clotting. As illustrated, fibrin polymerization increases over time when both thrombin and fibrinogen are combined with SARS-CoV-2 Spike-pseudotyped virions. Substantially less fibrin polymerization occurs when over time when thrombin and fibrinogen are combined but without virions that display SARS-CoV-2 Spike proteins. Fgg refers to human fibrinogen, while Th refers to thrombin with calcium chloride.

As illustrated in FIG. 6, the quantity of polymerized fibrinogen is greatest when pseudotyped SARS-CoV-2 Spike protein expressing virions are mixed with fibrinogen and thrombin. The amount of fibrin polymerization in the presence of thrombin and BALD non-Spike-expressing virions was no more than the amount of fibrinogen polymerization exhibited by the thrombin-fibrinogen mixture (FIG. 6).

Example 3: Anti-fibrin(ogen) Antibodies Inhibit Spike Virion Binding

This Example illustrates that anti-fibrin(ogen) antibodies can inhibit or prevent pseudotyped SARS-CoV-2 Spike protein expressing virions from binding and accumulating in lung tissues.

Mice (6 per group) were intravenously administered anti-Fibrin(ogen) 5B8 antibodies (30 mg/kg) or IgG2b antibodies (30 mg/kg; control). Twenty-four hours after antibody administration SARS-CoV-2 Spike pseudovirions were injected into the mice. Lung tissues were collected and sections were stained with 4',6-diamidino-2-phenylindole (DAPI; blue) as well as either labeled anti-spike antibodies (bright red) or labeled anti-Fibrin(ogen) antibodies (bright green). The quantities of SARS-CoV-2 Spike protein and fibrin(ogen) were determined by detecting the signals from the labeled antibodies from multiple microscopic fields in each of the six mice conditions.

Figure 7A:
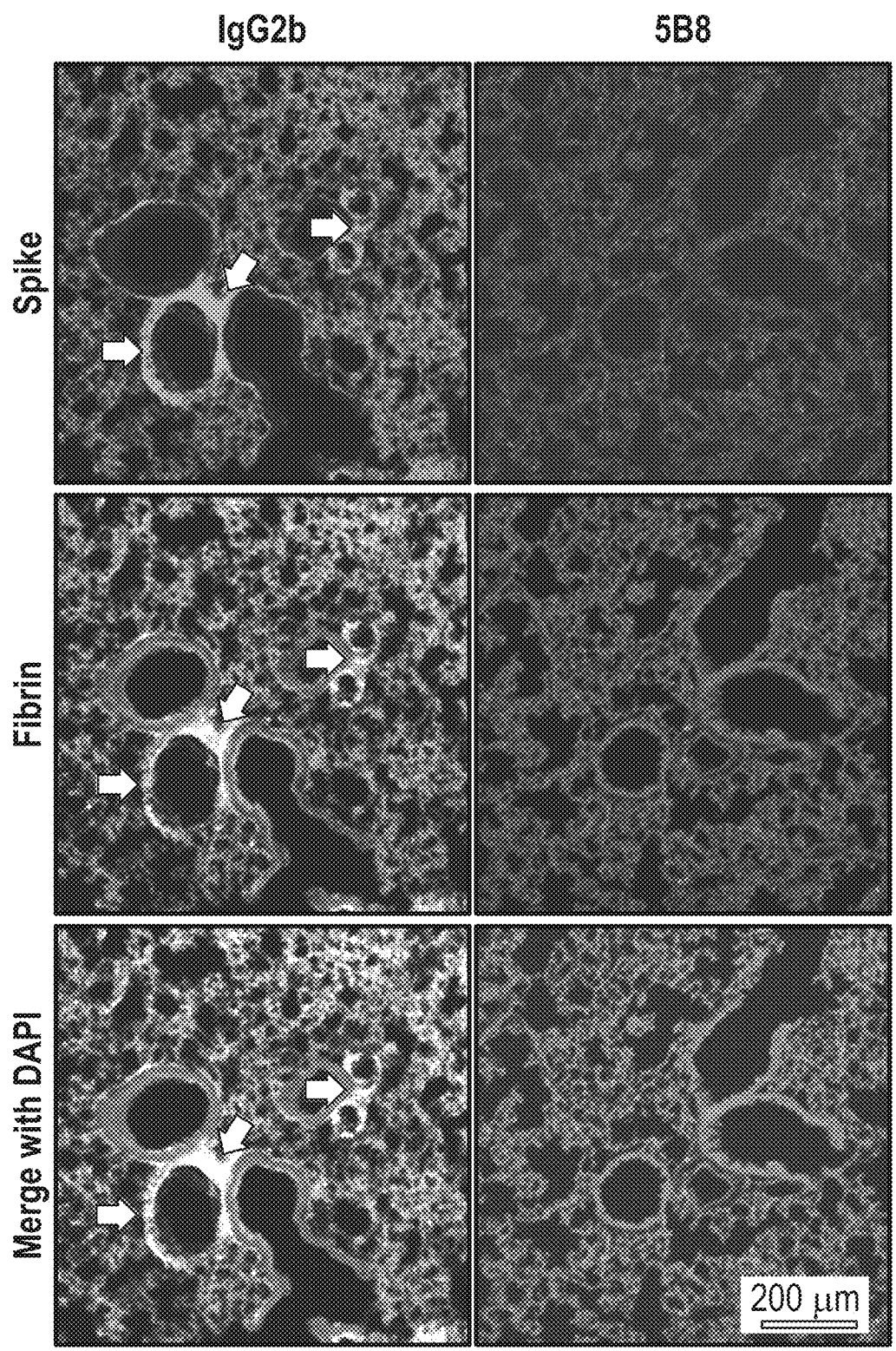

FIG. 7A shows images of the lung sections, demonstrating that treatment with 5B8 antibody, but not control IgG2b antibody, blocks fibrin and Spike co-deposition in the lungs of mice injected with Spike pseudotyped virions.

FIG. 7B graphically illustrates the quantity of SARS-CoV-2 Spike protein when the anti-Fibrin(ogen) 5B8 antibodies or the control IgG antibodies were administered. As shown, when the anti-Fibrin(ogen) 5B8 antibodies were administered, little or no SARS-CoV-2 Spike protein was deposited in the lung tissues.

FIG. 7C graphically illustrates the quantity of Fibrin (ogen) when the anti-Fibrin(ogen) 5B8 antibodies or the control IgG antibodies were administered. As shown, when the anti-Fibrin(ogen) 5B8 antibodies were administered, little or no fibrin(ogen) was deposited in the lung tissues.

These findings show that not only do 5B8 anti-Fibrin(gen) antibodies exert anti-inflammatory effects but they also prevent fibrin deposition, which is part of the clotting process.

Example 4: SpikemMay Increase Fibrin-Related Brain Inflammation

Fibrinogen is causally linked to the activation of macrophages and microglia in autoimmune and inflammatory diseases in the brain and periphery (Davalos & Akassoglou, *Semin Immunopathol* 34, 43-62 (2012); Petersen, Ryu, & Akassoglou, *Nat Rev Neurosci* 19, 283-301 (2018)). Fibrin is a driver of microglia-induced cognitive dysfunction (Merlini et al, *Neuron* 101, 1099-1108 (2019)) and is associated with perivascular-activated microglia and macrophages in brains of COVID-19 patients even without signs of infection (Lee et al., *N Engl Med* 384, 481-483 (2021)). Stereotactic injection of fibrinogen into the brains of WT mice is a model of fibrinogen-induced encephalomyelitis (Petersen, Ryu, & Akassoglou, *Nat Rev Neurosci* 19, 283-301 (2018))).

Co-injection of Spike pseudotyped virions and fibrinogen into the brains of wild type mice significantly increased fibrin-induced microglia activation (FIG. 8), indicating that the Spike protein and Spike protein-pseudotyped virions enhance the inflammatory function of fibrin in vivo.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:
1. A method comprising administering virions pseudotyped with SARS-CoV-2 Spike to one or more animals and detecting or measuring the physiological effects of the SARS-CoV-2 Spike protein expressing virions on at least one organ of the one or more animals.
2. The method of statement 1, further comprising repeatedly administering the virions pseudotyped with SARS-CoV-2 Spike to one or more of the animals.
3. The method of statement 1 or 2, further comprising administering a test agent to one or more of the animals.
4. The method of statement 1, 2 or 3, further comprising comparing the physiological effects to a control.
5. The method of statement 1-3 or 4, wherein the animal is a rodent.
6. The method of statement 5, wherein the rodent is a mouse, rat, or hamster.
7. The method of statement 1-5, or 6, wherein the animal is a thin-skulled animal.
8. The method of statement 1-6 or 7, wherein at least one of the organs is a lung, brain, gut, blood vessel, heart, or a combination thereof.
9. The method of statement 3-7 or 8, wherein the test agent is a small molecule, a polypeptide or an antibody.
10. The method of statement 9, wherein the antibody is a preparation of human antibodies or humanized antibodies.
11. The method of statement 9 or 10, wherein the antibody is an anti-fibrin antibody, an anti-fibrinogen antibody, or an anti-SARS-CoV-2 protein antibody.
12. The method of statement 11, wherein the anti-SARS-CoV-2 protein antibody is an anti-Spike protein antibody.
13. The method of statement 3-11 or 12, wherein the test agent can bind fibrin or a SARS-CoV-2 protein.
14. The method of statement 3-12 or 13, wherein the test agent can bind the SARS-CoV-2 Spike protein.
15. The method of statement 3-13 or 14, wherein the test agent is administered at the same time as the pseudotyped SARS-CoV-2 Spike protein virions, or at a time after the pseudotyped SARS-CoV-2 Spike protein virions are administered.
16. The method of statement 1-14 or 15, wherein the physiological effects are symptoms of the SARS-CoV-2 infection.
17. The method of statement 1-15 or 16, wherein the physiological effects comprise inflammation, oxidative stress, fibrin deposition, clot formation, or a combination thereof.
18. The method of statement 1-16 or 17, wherein measuring the physiological effects comprises measuring decreases or increases in inflammation within the subject compared to a control.
19. The method of statement 1-17, or 18, wherein measuring the physiological effects comprises measuring and/or quantifying inflammation in tissues with fibrin deposition compared to a control.
20. The method of statement 1-18, or 19, wherein measuring the physiological effects comprises measuring and/or quantifying inflammation in the subject's lung, heart, blood vessels, gut, brain, or a combination thereof compared to a control.
21. The method of statement 1-19, or 20, wherein measuring the physiological effects comprises measuring virion binding to fibrin or fibrinogen compared to a control.
22. The method of statement 1-20 or 21, wherein measuring the physiological effects comprises measuring SARS-CoV-2 Spike protein binding to fibrin or fibrinogen.
23. The method of statement 1-21 or 22, wherein measuring the physiological effects comprises measuring Mac-1 protein binding to fibrin or fibrinogen compared to the control.
24. The method of statement 1-22 or 23, wherein measuring the physiological effects comprises measuring whether inhibition of SARS-CoV-2 Spike protein binding, SARS-CoV-2 viral particle binding, or Mac-1 binding to the fibrin or fibrinogen is greater than 50% compared to the control.
25. The method of statement 24, wherein measuring the physiological effects comprises measuring whether virion or Spike protein binding to the fibrin or fibrinogen $\gamma$C domain is inhibited compared to a control.
26. The method of statement 1-24 or 25, wherein measuring the physiological effects comprises measuring binding of the virions or the Spike protein to a fibrin epitope with peptide sequence CKKTTMKIIPFNRLTIG (SEQ ID NO:12), B$\beta_{119-129}$ (YLLKDLWQKRQ, SEQ ID NO: 13), $\gamma_{163-181}$ (QSGLYFIKPLKANQQFLVY; SEQ ID NO:14), and/or $\gamma_{364-395}$ (DNGIIWATWKTRWYSMKKTTMKIIPFNRLTIG; SEQ ID NO:15) as a positive control or as compared to such binding of a negative control.
27. The method of statement 1-25 or 26, wherein the control is a negative control.

28. The method of statement 27, wherein the negative control is a control animal that did not receive SARS-CoV-2, or a control animal that received 'BALD' virions that do not express or display the SARS-CoV-2 Spike protein.
29. An animal model of SARS-CoV-2 infection comprising a rodent injected with pseudotyped SARS-CoV-2 Spike virions.
30. The animal model of statement 29, wherein the rodent is a mouse, rat, or hamster.
31. The animal model of statement 29 or 30, wherein the animal model exhibits physiological effects comprising one or more organs exhibiting inflammation, clots, oxidative stress, fibrin deposits, or a combination thereof compared to a control.
32. The animal model of statement 29, 30 or 31, wherein the animal model exhibits physiological effects comprising one or more organs having inflammation in tissues with fibrin deposition compared to a control.
33. The animal model of statement 29-31 or 32, wherein the control is a negative control.
34. The animal model of statement 33, wherein the negative control is a control animal that did not receive SARS-CoV-2, or a control animal that received 'BALD' virions that do not express or display the SARS-CoV-2. Spike protein.
35. The animal model of statement 29-33 or 34, further comprising a test agent.
36. The animal model of statement 35, wherein the test agent is administered at the same time as the pseudotyped SARS-CoV-2 Spike protein virions are administered, or at a time after the pseudotyped SARS-CoV-2 Spike protein virions are administered.

The specific methods and compositions described herein are representative of preferred embodiments and are exemplary and not intended as limitations on the scope of the invention, Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "a protein" or "a cell" includes a plurality of such nucleic acids, proteins, or cells (for example, a solution or dried preparation of nucleic acids or expression cassettes, a solution of proteins, or a population of cells), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A method comprising administering virions pseudotyped with SARS-CoV-2 Spike to a rodent and detecting or measuring physiological effects of the SARS-CoV-2 Spike protein on at least one organ of the rodent, wherein human ACE2 receptors are not present.

2. The method of claim 1, wherein the virions pseudotyped with SARS-CoV-2 Spike are administered repeatedly or continuously to the rodent.

3. The method of claim 1, further comprising administering a test agent to the rodent.

4. The method of claim 3, further comprising measuring physiological effects of the SARS-CoV-2 Spike after the test agent is administered.

5. The method of claim 1, wherein at least one of the organs is a lung, brain, gut, blood vessel, heart, or a combination thereof.

6. The method of claim 3, wherein the test agent is a small molecule, a polypeptide, or an antibody.

7. The method of claim 6, wherein the antibody is an anti-fibrin antibody, an anti-fibrinogen antibody, or an anti-SARS-CoV-2 protein antibody.

8. The method of claim 3, wherein the test agent can bind fibrin or a SARS-CoV-2 protein.

9. The method of claim 1, wherein the test agent is administered at the same time as the pseudotyped SARS-CoV-2 Spike protein virions, or at a time after the pseudotyped SARS-CoV-2 Spike protein virions are administered.

10. The method of claim 1, wherein the physiological effects are symptoms of the SARS-CoV-2 infection.

11. The method of claim 1, wherein the physiological effects comprise inflammation, oxidative stress, fibrin deposition, clots, clot formation, virion binding to fibrin or fibrinogen, SARS-CoV-2 Spike protein binding to fibrin or fibrinogen, Mac-1 protein binding to fibrin or fibrinogen, or a combination thereof.

12. The method of claim 3, wherein measuring the physiological effects after administering a test agent to the rodent comprises measuring whether the test agent reduces inflammation, oxidative stress, fibrin deposition, clot formation, virion binding to fibrin or fibrinogen, SARS-CoV-2 Spike protein binding to fibrin or fibrinogen, Mac-1 protein binding to fibrin or fibrinogen, or a combination thereof by more than 50% compared to a control.

13. The method of claim 12, wherein the control is a negative control.

14. The method of claim 1, wherein the rodent is a mouse, rat, or hamster.

\* \* \* \* \*

SEQUENCE LISTING

```
<160> NUMBER OF SEQ ID NOS: 34

<210> SEQ ID NO 1
<211> LENGTH: 1273
<212> TYPE: PRT
<213> ORGANISM: SARS CoV-2

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
```

```
            35                  40                  45
His Ser Thr Gln Asp Leu Phe Leu Pro Phe Phe Ser Asn Val Thr Trp
 50                  55                  60

Phe His Ala Ile His Val Ser Gly Thr Asn Gly Thr Lys Arg Phe Asp
 65                  70                  75                  80

Asn Pro Val Leu Pro Phe Asn Asp Gly Val Tyr Phe Ala Ser Thr Glu
                 85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
                115                 120                 125

Lys Val Cys Glu Phe Gln Phe Cys Asn Asp Pro Phe Leu Gly Val Tyr
            130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460
```

```
Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880
```

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
        900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270

<210> SEQ ID NO 2
<211> LENGTH: 254
<212> TYPE: PRT

<213> ORGANISM: SARS CoV-2

<400> SEQUENCE: 2

Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
            20                  25                  30

Val Ala Asp Tyr Ser Val Leu Tyr Asn Ser Ala Ser Phe Ser Thr Phe
        35                  40                  45

Lys Cys Tyr Gly Val Ser Pro Thr Lys Leu Asn Asp Leu Cys Phe Thr
    50                  55                  60

Asn Val Tyr Ala Asp Ser Phe Val Ile Arg Gly Asp Glu Val Arg Gln
65                  70                  75                  80

Ile Ala Pro Gly Gln Thr Gly Lys Ile Ala Asp Tyr Asn Tyr Lys Leu
                85                  90                  95

Pro Asp Asp Phe Thr Gly Cys Val Ile Ala Trp Asn Ser Asn Asn Leu
            100                 105                 110

Asp Ser Lys Val Gly Gly Asn Tyr Asn Tyr Leu Tyr Arg Leu Phe Arg
        115                 120                 125

Lys Ser Asn Leu Lys Pro Phe Glu Arg Asp Ile Ser Thr Glu Ile Tyr
    130                 135                 140

Gln Ala Gly Ser Thr Pro Cys Asn Gly Val Glu Gly Phe Asn Cys Tyr
145                 150                 155                 160

Phe Pro Leu Gln Ser Tyr Gly Phe Gln Pro Thr Asn Gly Val Gly Tyr
                165                 170                 175

Gln Pro Tyr Arg Val Val Val Leu Ser Phe Glu Leu Leu His Ala Pro
            180                 185                 190

Ala Thr Val Cys Gly Pro Lys Lys Ser Thr Asn Leu Val Lys Asn Lys
        195                 200                 205

Cys Val Asn Phe Asn Phe Asn Gly Leu Thr Gly Thr Gly Val Leu Thr
    210                 215                 220

Glu Ser Asn Lys Lys Phe Leu Pro Phe Gln Gln Phe Gly Arg Asp Ile
225                 230                 235                 240

Ala Asp Thr Thr Asp Ala Val Arg Asp Pro Gln Thr Leu Glu
                245                 250

<210> SEQ ID NO 3
<211> LENGTH: 610
<212> TYPE: PRT
<213> ORGANISM: SARS CoV-2

<400> SEQUENCE: 3

Cys Asp Ile Pro Ile Gly Ala Gly Ile Cys Ala Ser Tyr Gln Thr Gln
1               5                   10                  15

Thr Asn Ser Pro Arg Arg Ala Arg Ser Val Ala Ser Gln Ser Ile Ile
            20                  25                  30

Ala Tyr Thr Met Ser Leu Gly Ala Glu Asn Ser Val Ala Tyr Ser Asn
        35                  40                  45

Asn Ser Ile Ala Ile Pro Thr Asn Phe Thr Ile Ser Val Thr Thr Glu
    50                  55                  60

Ile Leu Pro Val Ser Met Thr Lys Thr Ser Val Asp Cys Thr Met Tyr
65                  70                  75                  80

Ile Cys Gly Asp Ser Thr Glu Cys Ser Asn Leu Leu Leu Gln Tyr Gly
                85                  90                  95

Ser Phe Cys Thr Gln Leu Asn Arg Ala Leu Thr Gly Ile Ala Val Glu

```
                100             105             110
        Gln Asp Lys Asn Thr Gln Glu Val Phe Ala Gln Val Lys Gln Ile Tyr
                    115                 120                 125
        Lys Thr Pro Pro Ile Lys Asp Phe Gly Gly Phe Asn Phe Ser Gln Ile
                    130                 135                 140
        Leu Pro Asp Pro Ser Lys Pro Ser Lys Arg Ser Phe Ile Glu Asp Leu
        145                 150                 155                 160
        Leu Phe Asn Lys Val Thr Leu Ala Asp Ala Gly Phe Ile Lys Gln Tyr
                            165                 170                 175
        Gly Asp Cys Leu Gly Asp Ile Ala Ala Arg Asp Leu Ile Cys Ala Gln
                        180                 185                 190
        Lys Phe Asn Gly Leu Thr Val Leu Pro Pro Leu Leu Thr Asp Glu Met
                    195                 200                 205
        Ile Ala Gln Tyr Thr Ser Ala Leu Leu Ala Gly Thr Ile Thr Ser Gly
                    210                 215                 220
        Trp Thr Phe Gly Ala Gly Ala Ala Leu Gln Ile Pro Phe Ala Met Gln
        225                 230                 235                 240
        Met Ala Tyr Arg Phe Asn Gly Ile Gly Val Thr Gln Asn Val Leu Tyr
                            245                 250                 255
        Glu Asn Gln Lys Leu Ile Ala Asn Gln Phe Asn Ser Ala Ile Gly Lys
                        260                 265                 270
        Ile Gln Asp Ser Leu Ser Ser Thr Ala Ser Ala Leu Gly Lys Leu Gln
                    275                 280                 285
        Asp Val Val Asn Gln Asn Ala Gln Ala Leu Asn Thr Leu Val Lys Gln
                    290                 295                 300
        Leu Ser Ser Asn Phe Gly Ala Ile Ser Ser Val Leu Asn Asp Ile Leu
        305                 310                 315                 320
        Ser Arg Leu Asp Lys Val Glu Ala Glu Val Gln Ile Asp Arg Leu Ile
                            325                 330                 335
        Thr Gly Arg Leu Gln Ser Leu Gln Thr Tyr Val Thr Gln Gln Leu Ile
                        340                 345                 350
        Arg Ala Ala Glu Ile Arg Ala Ser Ala Asn Leu Ala Ala Thr Lys Met
                    355                 360                 365
        Ser Glu Cys Val Leu Gly Gln Ser Lys Arg Val Asp Phe Cys Gly Lys
                    370                 375                 380
        Gly Tyr His Leu Met Ser Phe Pro Gln Ser Ala Pro His Gly Val Val
        385                 390                 395                 400
        Phe Leu His Val Thr Tyr Val Pro Ala Gln Glu Lys Asn Phe Thr Thr
                            405                 410                 415
        Ala Pro Ala Ile Cys His Asp Gly Lys Ala His Phe Pro Arg Glu Gly
                        420                 425                 430
        Val Phe Val Ser Asn Gly Thr His Trp Phe Val Thr Gln Arg Asn Phe
                    435                 440                 445
        Tyr Glu Pro Gln Ile Ile Thr Thr Asp Asn Thr Phe Val Ser Gly Asn
                    450                 455                 460
        Cys Asp Val Val Ile Gly Ile Val Asn Asn Thr Val Tyr Asp Pro Leu
        465                 470                 475                 480
        Gln Pro Glu Leu Asp Ser Phe Lys Glu Glu Leu Asp Lys Tyr Phe Lys
                            485                 490                 495
        Asn His Thr Ser Pro Asp Val Asp Leu Gly Asp Ile Ser Gly Ile Asn
                        500                 505                 510
        Ala Ser Val Val Asn Ile Gln Lys Glu Ile Asp Arg Leu Asn Glu Val
                    515                 520                 525
```

```
Ala Lys Asn Leu Asn Glu Ser Leu Ile Asp Leu Gln Glu Leu Gly Lys
    530                 535                 540

Tyr Glu Gln Tyr Ile Lys Trp Pro Trp Tyr Ile Trp Leu Gly Phe Ile
545                 550                 555                 560

Ala Gly Leu Ile Ala Ile Val Met Val Thr Ile Met Leu Cys Cys Met
                565                 570                 575

Thr Ser Cys Cys Ser Cys Leu Lys Gly Cys Cys Ser Cys Gly Ser Cys
            580                 585                 590

Cys Lys Phe Asp Glu Asp Asp Ser Glu Pro Val Leu Lys Gly Val Lys
        595                 600                 605

Leu His
    610
```

```
<210> SEQ ID NO 4
<211> LENGTH: 1282
<212> TYPE: PRT
<213> ORGANISM: Artificial Sequence
<220> FEATURE:
<223> OTHER INFORMATION: A synthetic sequence

<400> SEQUENCE: 4

Met Phe Leu Leu Thr Thr Lys Arg Thr Met Phe Val Phe Leu Val Leu
1               5                   10                  15

Leu Pro Leu Val Ser Ser Gln Cys Val Asn Leu Thr Thr Arg Thr Gln
                20                  25                  30

Leu Pro Pro Ala Tyr Thr Asn Ser Phe Thr Arg Gly Val Tyr Tyr Pro
            35                  40                  45

Asp Lys Val Phe Arg Ser Ser Val Leu His Ser Thr Gln Asp Leu Phe
50                  55                  60

Leu Pro Phe Phe Ser Asn Val Thr Trp Phe His Ala Ile His Val Ser
65                  70                  75                  80

Gly Thr Asn Gly Thr Lys Arg Phe Asp Asn Pro Val Leu Pro Phe Asn
                85                  90                  95

Asp Gly Val Tyr Phe Ala Ser Thr Glu Lys Ser Asn Ile Ile Arg Gly
            100                 105                 110

Trp Ile Phe Gly Thr Thr Leu Asp Ser Lys Thr Gln Ser Leu Leu Ile
        115                 120                 125

Val Asn Asn Ala Thr Asn Val Val Ile Lys Val Cys Glu Phe Gln Phe
    130                 135                 140

Cys Asn Asp Pro Phe Leu Gly Val Tyr Tyr His Lys Asn Asn Lys Ser
145                 150                 155                 160

Trp Met Glu Ser Glu Phe Arg Val Tyr Ser Ser Ala Asn Asn Cys Thr
                165                 170                 175

Phe Glu Tyr Val Ser Gln Pro Phe Leu Met Asp Leu Glu Gly Lys Gln
            180                 185                 190

Gly Asn Phe Lys Asn Leu Arg Glu Phe Val Phe Lys Asn Ile Asp Gly
        195                 200                 205

Tyr Phe Lys Ile Tyr Ser Lys His Thr Pro Ile Asn Leu Val Arg Asp
    210                 215                 220

Leu Pro Gln Gly Phe Ser Ala Leu Glu Pro Leu Val Asp Leu Pro Ile
225                 230                 235                 240

Gly Ile Asn Ile Thr Arg Phe Gln Thr Leu Leu Ala Leu His Arg Ser
                245                 250                 255

Tyr Leu Thr Pro Gly Asp Ser Ser Ser Gly Trp Thr Ala Gly Ala Ala
            260                 265                 270
```

```
Ala Tyr Tyr Val Gly Tyr Leu Gln Pro Arg Thr Phe Leu Leu Lys Tyr
    275                 280                 285

Asn Glu Asn Gly Thr Ile Thr Asp Ala Val Asp Cys Ala Leu Asp Pro
290                 295                 300

Leu Ser Glu Thr Lys Cys Thr Leu Lys Ser Phe Thr Val Glu Lys Gly
305                 310                 315                 320

Ile Tyr Gln Thr Ser Asn Phe Arg Val Gln Pro Thr Glu Ser Ile Val
                325                 330                 335

Arg Phe Pro Asn Ile Thr Asn Leu Cys Pro Phe Gly Glu Val Phe Asn
                340                 345                 350

Ala Thr Arg Phe Ala Ser Val Tyr Ala Trp Asn Arg Lys Arg Ile Ser
            355                 360                 365

Asn Cys Val Ala Asp Tyr Ser Val Leu Tyr Asn Ser Ala Ser Phe Ser
370                 375                 380

Thr Phe Lys Cys Tyr Gly Val Ser Pro Thr Lys Leu Asn Asp Leu Cys
385                 390                 395                 400

Phe Thr Asn Val Tyr Ala Asp Ser Phe Val Ile Arg Gly Asp Glu Val
                405                 410                 415

Arg Gln Ile Ala Pro Gly Gln Thr Gly Lys Ile Ala Asp Tyr Asn Tyr
                420                 425                 430

Lys Leu Pro Asp Asp Phe Thr Gly Cys Val Ile Ala Trp Asn Ser Asn
            435                 440                 445

Asn Leu Asp Ser Lys Val Gly Gly Asn Tyr Asn Tyr Leu Tyr Arg Leu
450                 455                 460

Phe Arg Lys Ser Asn Leu Lys Pro Phe Glu Arg Asp Ile Ser Thr Glu
465                 470                 475                 480

Ile Tyr Gln Ala Gly Ser Thr Pro Cys Asn Gly Val Glu Gly Phe Asn
                485                 490                 495

Cys Tyr Phe Pro Leu Gln Ser Tyr Gly Phe Gln Pro Thr Asn Gly Val
                500                 505                 510

Gly Tyr Gln Pro Tyr Arg Val Val Val Leu Ser Phe Glu Leu Leu His
            515                 520                 525

Ala Pro Ala Thr Val Cys Gly Pro Lys Lys Ser Thr Asn Leu Val Lys
530                 535                 540

Asn Lys Cys Val Asn Phe Asn Phe Asn Gly Leu Thr Gly Thr Gly Val
545                 550                 555                 560

Leu Thr Glu Ser Asn Lys Lys Phe Leu Pro Phe Gln Gln Phe Gly Arg
                565                 570                 575

Asp Ile Ala Asp Thr Thr Asp Ala Val Arg Asp Pro Gln Thr Leu Glu
            580                 585                 590

Ile Leu Asp Ile Thr Pro Cys Ser Phe Gly Gly Val Ser Val Ile Thr
            595                 600                 605

Pro Gly Thr Asn Thr Ser Asn Gln Val Ala Val Leu Tyr Gln Asp Val
610                 615                 620

Asn Cys Thr Glu Val Pro Val Ala Ile His Ala Asp Gln Leu Thr Pro
625                 630                 635                 640

Thr Trp Arg Val Tyr Ser Thr Gly Ser Asn Val Phe Gln Thr Arg Ala
                645                 650                 655

Gly Cys Leu Ile Gly Ala Glu His Val Asn Asn Ser Tyr Glu Cys Asp
            660                 665                 670

Ile Pro Ile Gly Ala Gly Ile Cys Ala Ser Tyr Gln Thr Gln Thr Asn
            675                 680                 685
```

-continued

```
Ser Pro Arg Arg Ala Arg Ser Val Ala Ser Gln Ser Ile Ile Ala Tyr
    690                 695                 700

Thr Met Ser Leu Gly Ala Glu Asn Ser Val Ala Tyr Ser Asn Asn Ser
705                 710                 715                 720

Ile Ala Ile Pro Thr Asn Phe Thr Ile Ser Val Thr Thr Glu Ile Leu
                725                 730                 735

Pro Val Ser Met Thr Lys Thr Ser Val Asp Cys Thr Met Tyr Ile Cys
                740                 745                 750

Gly Asp Ser Thr Glu Cys Ser Asn Leu Leu Leu Gln Tyr Gly Ser Phe
                755                 760                 765

Cys Thr Gln Leu Asn Arg Ala Leu Thr Gly Ile Ala Val Glu Gln Asp
    770                 775                 780

Lys Asn Thr Gln Glu Val Phe Ala Gln Val Lys Gln Ile Tyr Lys Thr
785                 790                 795                 800

Pro Pro Ile Lys Asp Phe Gly Gly Phe Asn Phe Ser Gln Ile Leu Pro
                805                 810                 815

Asp Pro Ser Lys Pro Ser Lys Arg Ser Phe Ile Glu Asp Leu Leu Phe
                820                 825                 830

Asn Lys Val Thr Leu Ala Asp Ala Gly Phe Ile Lys Gln Tyr Gly Asp
                835                 840                 845

Cys Leu Gly Asp Ile Ala Ala Arg Asp Leu Ile Cys Ala Gln Lys Phe
    850                 855                 860

Asn Gly Leu Thr Val Leu Pro Pro Leu Leu Thr Asp Glu Met Ile Ala
865                 870                 875                 880

Gln Tyr Thr Ser Ala Leu Leu Ala Gly Thr Ile Thr Ser Gly Trp Thr
                885                 890                 895

Phe Gly Ala Gly Ala Ala Leu Gln Ile Pro Phe Ala Met Gln Met Ala
                900                 905                 910

Tyr Arg Phe Asn Gly Ile Gly Val Thr Gln Asn Val Leu Tyr Glu Asn
                915                 920                 925

Gln Lys Leu Ile Ala Asn Gln Phe Asn Ser Ala Ile Gly Lys Ile Gln
    930                 935                 940

Asp Ser Leu Ser Ser Thr Ala Ser Ala Leu Gly Lys Leu Gln Asp Val
945                 950                 955                 960

Val Asn Gln Asn Ala Gln Ala Leu Asn Thr Leu Val Lys Gln Leu Ser
                965                 970                 975

Ser Asn Phe Gly Ala Ile Ser Ser Val Leu Asn Asp Ile Leu Ser Arg
                980                 985                 990

Leu Asp Lys Val Glu Ala Glu Val Gln Ile Asp Arg Leu Ile Thr Gly
    995                 1000                1005

Arg Leu Gln Ser Leu Gln Thr Tyr Val Thr Gln Gln Leu Ile Arg Ala
    1010                1015                1020

Ala Glu Ile Arg Ala Ser Ala Asn Leu Ala Ala Thr Lys Met Ser Glu
1025                1030                1035                1040

Cys Val Leu Gly Gln Ser Lys Arg Val Asp Phe Cys Gly Lys Gly Tyr
                1045                1050                1055

His Leu Met Ser Phe Pro Gln Ser Ala Pro His Gly Val Val Phe Leu
                1060                1065                1070

His Val Thr Tyr Val Pro Ala Gln Glu Lys Asn Phe Thr Thr Ala Pro
                1075                1080                1085

Ala Ile Cys His Asp Gly Lys Ala His Phe Pro Arg Glu Gly Val Phe
    1090                1095                1100

Val Ser Asn Gly Thr His Trp Phe Val Thr Gln Arg Asn Phe Tyr Glu
```

```
                    1105                1110                1115                1120
        Pro Gln Ile Ile Thr Thr Asp Asn Thr Phe Val Ser Gly Asn Cys Asp
                        1125                1130                1135

Val Val Ile Gly Ile Val Asn Asn Thr Val Tyr Asp Pro Leu Gln Pro
                        1140                1145                1150

Glu Leu Asp Ser Phe Lys Glu Leu Asp Lys Tyr Phe Lys Asn His
                        1155                1160                1165

Thr Ser Pro Asp Val Asp Leu Gly Asp Ile Ser Gly Ile Asn Ala Ser
                        1170                1175                1180

Val Val Asn Ile Gln Lys Glu Ile Asp Arg Leu Asn Glu Val Ala Lys
        1185                1190                1195                1200

Asn Leu Asn Glu Ser Leu Ile Asp Leu Gln Glu Leu Gly Lys Tyr Glu
                        1205                1210                1215

Gln Tyr Ile Lys Trp Pro Trp Tyr Ile Trp Leu Gly Phe Ile Ala Gly
                        1220                1225                1230

Leu Ile Ala Ile Val Met Val Thr Ile Met Leu Cys Cys Met Thr Ser
                        1235                1240                1245

Cys Cys Ser Cys Leu Lys Gly Cys Cys Ser Cys Gly Ser Cys Cys Lys
                        1250                1255                1260

Phe Asp Glu Asp Asp Ser Glu Pro Val Leu Lys Gly Val Lys Leu His
        1265                1270                1275                1280

Tyr Thr

<210> SEQ ID NO 5
<211> LENGTH: 1273
<212> TYPE: PRT
<213> ORGANISM: Artificial Sequence
<220> FEATURE:
<223> OTHER INFORMATION: A synthetic sequence

<400> SEQUENCE: 5

Met Phe Val Phe Leu Val Leu Leu Pro Leu Val Ser Ser Gln Cys Val
        1                5                  10                  15

Asn Leu Thr Thr Arg Thr Gln Leu Pro Pro Ala Tyr Thr Asn Ser Phe
                        20                  25                  30

Thr Arg Gly Val Tyr Tyr Pro Asp Lys Val Phe Arg Ser Ser Val Leu
                        35                  40                  45

His Ser Thr Gln Asp Leu Phe Leu Pro Phe Phe Ser Asn Val Thr Trp
                        50                  55                  60

Phe His Ala Ile His Val Ser Gly Thr Asn Gly Thr Lys Arg Phe Asp
        65                  70                  75                  80

Asn Pro Val Leu Pro Phe Asn Asp Gly Val Tyr Phe Ala Ser Thr Glu
                        85                  90                  95

Lys Ser Asn Ile Ile Arg Gly Trp Ile Phe Gly Thr Thr Leu Asp Ser
                        100                 105                 110

Lys Thr Gln Ser Leu Leu Ile Val Asn Asn Ala Thr Asn Val Val Ile
                        115                 120                 125

Lys Val Cys Glu Phe Gln Phe Cys Asn Asp Pro Phe Leu Gly Val Tyr
                        130                 135                 140

Tyr His Lys Asn Asn Lys Ser Trp Met Glu Ser Glu Phe Arg Val Tyr
        145                 150                 155                 160

Ser Ser Ala Asn Asn Cys Thr Phe Glu Tyr Val Ser Gln Pro Phe Leu
                        165                 170                 175

Met Asp Leu Glu Gly Lys Gln Gly Asn Phe Lys Asn Leu Arg Glu Phe
                        180                 185                 190
```

```
Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
            210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
            290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Leu Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605
```

-continued

Ala Val Leu Tyr Gln Asp Val Asn Cys Thr Glu Val Pro Val Ala Ile
610              615              620

His Ala Asp Gln Leu Thr Pro Thr Trp Arg Val Tyr Ser Thr Gly Ser
625              630              635              640

Asn Val Phe Gln Thr Arg Ala Gly Cys Leu Ile Gly Ala Glu His Val
            645              650              655

Asn Asn Ser Tyr Glu Cys Asp Ile Pro Ile Gly Ala Gly Ile Cys Ala
            660              665              670

Ser Tyr Gln Thr Gln Thr Asn Ser Pro Arg Arg Ala Arg Ser Val Ala
            675              680              685

Ser Gln Ser Ile Ile Ala Tyr Thr Met Ser Leu Gly Ala Glu Asn Ser
690              695              700

Val Ala Tyr Ser Asn Asn Ser Ile Ala Ile Pro Thr Asn Phe Thr Ile
705              710              715              720

Ser Val Thr Thr Glu Ile Leu Pro Val Ser Met Thr Lys Thr Ser Val
            725              730              735

Asp Cys Thr Met Tyr Ile Cys Gly Asp Ser Thr Glu Cys Ser Asn Leu
            740              745              750

Leu Leu Gln Tyr Gly Ser Phe Cys Thr Gln Leu Asn Arg Ala Leu Thr
            755              760              765

Gly Ile Ala Val Glu Gln Asp Lys Asn Thr Gln Glu Val Phe Ala Gln
770              775              780

Val Lys Gln Ile Tyr Lys Thr Pro Pro Ile Lys Asp Phe Gly Gly Phe
785              790              795              800

Asn Phe Ser Gln Ile Leu Pro Asp Pro Ser Lys Pro Ser Lys Arg Ser
            805              810              815

Phe Ile Glu Asp Leu Leu Phe Asn Lys Val Thr Leu Ala Asp Ala Gly
            820              825              830

Phe Ile Lys Gln Tyr Gly Asp Cys Leu Gly Asp Ile Ala Ala Arg Asp
            835              840              845

Leu Ile Cys Ala Gln Lys Phe Asn Gly Leu Thr Val Leu Pro Pro Leu
850              855              860

Leu Thr Asp Glu Met Ile Ala Gln Tyr Thr Ser Ala Leu Leu Ala Gly
865              870              875              880

Thr Ile Thr Ser Gly Trp Thr Phe Gly Ala Gly Ala Ala Leu Gln Ile
            885              890              895

Pro Phe Ala Met Gln Met Ala Tyr Arg Phe Asn Gly Ile Gly Val Thr
            900              905              910

Gln Asn Val Leu Tyr Glu Asn Gln Lys Leu Ile Ala Asn Gln Phe Asn
            915              920              925

Ser Ala Ile Gly Lys Ile Gln Asp Ser Leu Ser Ser Thr Ala Ser Ala
930              935              940

Leu Gly Lys Leu Gln Asp Val Val Asn Gln Asn Ala Gln Ala Leu Asn
945              950              955              960

Thr Leu Val Lys Gln Leu Ser Ser Asn Phe Gly Ala Ile Ser Ser Val
            965              970              975

Leu Asn Asp Ile Leu Ser Arg Leu Asp Lys Val Glu Ala Glu Val Gln
            980              985              990

Ile Asp Arg Leu Ile Thr Gly Arg Leu Gln Ser Leu Gln Thr Tyr Val
            995              1000             1005

Thr Gln Gln Leu Ile Arg Ala Ala Glu Ile Arg Ala Ser Ala Asn Leu
1010             1015             1020

Ala Ala Thr Lys Met Ser Glu Cys Val Leu Gly Gln Ser Lys Arg Val

-continued

```
            1025                1030                1035                1040
Asp Phe Cys Gly Lys Gly Tyr His Leu Met Ser Phe Pro Gln Ser Ala
                1045                1050                1055
Pro His Gly Val Val Phe Leu His Val Thr Tyr Val Pro Ala Gln Glu
                1060                1065                1070
Lys Asn Phe Thr Thr Ala Pro Ala Ile Cys His Asp Gly Lys Ala His
                1075                1080                1085
Phe Pro Arg Glu Gly Val Phe Val Ser Asn Gly Thr His Trp Phe Val
                1090                1095                1100
Thr Gln Arg Asn Phe Tyr Glu Pro Gln Ile Ile Thr Thr Asp Asn Thr
1105                1110                1115                1120
Phe Val Ser Gly Asn Cys Asp Val Val Ile Gly Ile Val Asn Asn Thr
                1125                1130                1135
Val Tyr Asp Pro Leu Gln Pro Glu Leu Asp Ser Phe Lys Glu Glu Leu
                1140                1145                1150
Asp Lys Tyr Phe Lys Asn His Thr Ser Pro Asp Val Asp Leu Gly Asp
                1155                1160                1165
Ile Ser Gly Ile Asn Ala Ser Val Val Asn Ile Gln Lys Glu Ile Asp
                1170                1175                1180
Arg Leu Asn Glu Val Ala Lys Asn Leu Asn Glu Ser Leu Ile Asp Leu
1185                1190                1195                1200
Gln Glu Leu Gly Lys Tyr Glu Gln Tyr Ile Lys Trp Pro Trp Tyr Ile
                1205                1210                1215
Trp Leu Gly Phe Ile Ala Gly Leu Ile Ala Ile Val Met Val Thr Ile
                1220                1225                1230
Met Leu Cys Cys Met Thr Ser Cys Cys Ser Cys Leu Lys Gly Cys Cys
                1235                1240                1245
Ser Cys Gly Ser Cys Cys Lys Phe Asp Glu Asp Ser Glu Pro Val
                1250                1255                1260
Leu Lys Gly Val Lys Leu His Tyr Thr
1265                1270

<210> SEQ ID NO 6
<211> LENGTH: 1273
<212> TYPE: PRT
<213> ORGANISM: Artificial Sequence
<220> FEATURE:
<223> OTHER INFORMATION: A synthetic sequence

<400> SEQUENCE: 6

Met Phe Val Phe Leu Val Leu Leu Pro Leu Val Ser Ser Gln Cys Val
1               5                   10                  15
Asn Leu Thr Thr Arg Ala Gln Leu Pro Pro Ala Tyr Thr Asn Ser Phe
                20                  25                  30
Thr Arg Gly Val Tyr Tyr Pro Asp Lys Val Phe Arg Ser Ser Val Leu
            35                  40                  45
His Ser Thr Gln Asp Leu Phe Leu Pro Phe Phe Ser Asn Val Thr Trp
        50                  55                  60
Phe His Ala Ile His Val Ser Gly Thr Asn Gly Thr Lys Arg Phe Asp
65                  70                  75                  80
Asn Pro Val Leu Pro Phe Asn Asp Gly Val Tyr Phe Ala Ser Thr Glu
                85                  90                  95
Lys Ser Asn Ile Ile Arg Gly Trp Ile Phe Gly Thr Thr Leu Asp Ser
                100                 105                 110
Lys Thr Gln Ser Leu Leu Ile Val Asn Asn Ala Thr Asn Val Val Ile
```

-continued

```
            115                 120                 125
Lys Val Cys Glu Phe Gln Phe Cys Asn Asp Pro Phe Leu Gly Val Tyr
            130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540
```

```
Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960
```

```
Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
        980                 985                 990

Ile Asp Arg Leu Ile Thr Gly Arg Leu Gln Ser Leu Gln Thr Tyr Val
        995                1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
            1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
            1075                1080                1085

Phe Pro Arg Glu Gly Val Phe Val Ser Asn Gly Thr His Trp Phe Val
        1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
            1125                1130                1135

Val Tyr Asp Pro Leu Gln Pro Glu Leu Asp Ser Phe Lys Glu Glu Leu
        1140                1145                1150

Asp Lys Tyr Phe Lys Asn His Thr Ser Pro Asp Val Asp Leu Gly Asp
            1155                1160                1165

Ile Ser Gly Ile Asn Ala Ser Val Val Asn Ile Gln Lys Glu Ile Asp
        1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
            1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
            1235                1240                1245

Ser Cys Gly Ser Cys Cys Lys Phe Asp Glu Asp Asp Ser Glu Pro Val
        1250                1255                1260

Leu Lys Gly Val Lys Leu His Tyr Thr
1265                1270

<210> SEQ ID NO 7
<211> LENGTH: 1273
<212> TYPE: PRT
<213> ORGANISM: Artificial Sequence
<220> FEATURE:
<223> OTHER INFORMATION: A synthetic sequence

<400> SEQUENCE: 7

Met Phe Val Phe Leu Val Leu Leu Pro Leu Val Ser Ser Gln Cys Val
1               5                   10                  15

Asn Leu Thr Thr Arg Ile Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45
```

```
His Ser Thr Gln Asp Leu Phe Leu Pro Phe Phe Ser Asn Val Thr Trp
 50                  55                  60

Phe His Ala Ile His Val Ser Gly Thr Asn Gly Thr Lys Arg Phe Asp
 65                  70                  75                  80

Asn Pro Val Leu Pro Phe Asn Asp Gly Val Tyr Phe Ala Ser Thr Glu
                 85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
    195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
    275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
    355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
    435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
```

```
            465                 470                 475                 480
Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
                530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
                610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
                690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
                850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895
```

```
Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270

<210> SEQ ID NO 8
<211> LENGTH: 1273
<212> TYPE: PRT
<213> ORGANISM: Artificial Sequence
<220> FEATURE:
```

-continued

<223> OTHER INFORMATION: A synthetic sequence

<400> SEQUENCE: 8

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Leu Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400
```

-continued

```
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
            420                 425                 430
Val Ile Ala Trp Asn Ser Asn Asn Leu Asp Ser Lys Val Gly Gly Asn
            435                 440                 445
Tyr Asn Tyr Leu Tyr Arg Leu Phe Arg Lys Ser Asn Leu Lys Pro Phe
        450                 455                 460
Glu Arg Asp Ile Ser Thr Glu Ile Tyr Gln Ala Gly Ser Thr Pro Cys
465                 470                 475                 480
Asn Gly Val Glu Gly Phe Asn Cys Tyr Phe Pro Leu Gln Ser Tyr Gly
                485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
            515                 520                 525
Lys Ser Thr Asn Leu Val Lys Asn Lys Cys Val Asn Phe Asn Phe Asn
        530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
                565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
            595                 600                 605
Ala Val Leu Tyr Gln Asp Val Asn Cys Thr Glu Val Pro Val Ala Ile
        610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
                645                 650                 655
Asn Asn Ser Tyr Glu Cys Asp Ile Pro Ile Gly Ala Gly Ile Cys Ala
            660                 665                 670
Ser Tyr Gln Thr Gln Thr Asn Ser Pro Arg Arg Ala Arg Ser Val Ala
            675                 680                 685
Ser Gln Ser Ile Ile Ala Tyr Thr Met Ser Leu Gly Ala Glu Asn Ser
        690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
                725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
        755                 760                 765
Gly Ile Ala Val Glu Gln Asp Lys Asn Thr Gln Glu Val Phe Ala Gln
    770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
                805                 810                 815
Phe Ile Glu Asp Leu Leu Phe Asn Lys Val Thr Leu Ala Asp Ala Gly
```

```
                820                 825                 830
Phe Ile Lys Gln Tyr Gly Asp Cys Leu Gly Asp Ile Ala Ala Arg Asp
            835                 840                 845
Leu Ile Cys Ala Gln Lys Phe Asn Gly Leu Thr Val Leu Pro Pro Leu
850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
                885                 890                 895
Pro Phe Ala Met Gln Met Ala Tyr Arg Phe Asn Gly Ile Gly Val Thr
            900                 905                 910
Gln Asn Val Leu Tyr Glu Asn Gln Lys Leu Ile Ala Asn Gln Phe Asn
        915                 920                 925
Ser Ala Ile Gly Lys Ile Gln Asp Ser Leu Ser Ser Thr Ala Ser Ala
            930                 935                 940
Leu Gly Lys Leu Gln Asp Val Val Asn Gln Asn Ala Gln Ala Leu Asn
945                 950                 955                 960
Thr Leu Val Lys Gln Leu Ser Ser Asn Phe Gly Ala Ile Ser Ser Val
                965                 970                 975
Leu Asn Asp Ile Leu Ser Arg Leu Asp Lys Val Glu Ala Glu Val Gln
            980                 985                 990
Ile Asp Arg Leu Ile Thr Gly Arg Leu Gln Ser Leu Gln Thr Tyr Val
        995                 1000                1005
Thr Gln Gln Leu Ile Arg Ala Ala Glu Ile Arg Ala Ser Ala Asn Leu
        1010                1015                1020
Ala Ala Thr Lys Met Ser Glu Cys Val Leu Gly Gln Ser Lys Arg Val
1025                1030                1035                1040
Asp Phe Cys Gly Lys Gly Tyr His Leu Met Ser Phe Pro Gln Ser Ala
            1045                1050                1055
Pro His Gly Val Val Phe Leu His Val Thr Tyr Val Pro Ala Gln Glu
            1060                1065                1070
Lys Asn Phe Thr Thr Ala Pro Ala Ile Cys His Asp Gly Lys Ala His
            1075                1080                1085
Phe Pro Arg Glu Gly Val Phe Val Ser Asn Gly Thr His Trp Phe Val
            1090                1095                1100
Thr Gln Arg Asn Phe Tyr Glu Pro Gln Ile Ile Thr Thr Asp Asn Thr
1105                1110                1115                1120
Phe Val Ser Gly Asn Cys Asp Val Val Ile Gly Ile Val Asn Asn Thr
            1125                1130                1135
Val Tyr Asp Pro Leu Gln Pro Glu Leu Asp Ser Phe Lys Glu Glu Leu
            1140                1145                1150
Asp Lys Tyr Phe Lys Asn His Thr Ser Pro Asp Val Asp Leu Gly Asp
            1155                1160                1165
Ile Ser Gly Ile Asn Ala Ser Val Val Asn Ile Gln Lys Glu Ile Asp
            1170                1175                1180
Arg Leu Asn Glu Val Ala Lys Asn Leu Asn Glu Ser Leu Ile Asp Leu
1185                1190                1195                1200
Gln Glu Leu Gly Lys Tyr Glu Gln Tyr Ile Lys Trp Pro Trp Tyr Ile
            1205                1210                1215
Trp Leu Gly Phe Ile Ala Gly Leu Ile Ala Ile Val Met Val Thr Ile
            1220                1225                1230
Met Leu Cys Cys Met Thr Ser Cys Cys Ser Cys Leu Lys Gly Cys Cys
            1235                1240                1245
```

Ser Cys Gly Ser Cys Cys Lys Phe Asp Glu Asp Ser Glu Pro Val
1250                1255                1260

Leu Lys Gly Val Lys Leu His Tyr Thr
1265                1270

<210> SEQ ID NO 9
<211> LENGTH: 1310
<212> TYPE: PRT
<213> ORGANISM: Artificial Sequence
<220> FEATURE:
<223> OTHER INFORMATION: A synthetic sequence

<400> SEQUENCE: 9

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
            595                 600                 605

Ala Val Leu Tyr Gln Gly Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750
```

-continued

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
                1060                1065                1070

Lys Asn Phe Thr Thr Ala Pro Ala Ile Cys His Asp Gly Lys Ala His
            1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp

```
                    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                    1205                1210                1215

Trp Leu Gly Phe Ile Ala Gly Leu Ile Ala Ile Val Met Val Thr Ile
                    1220                1225                1230

Met Leu Cys Cys Met Thr Ser Cys Cys Ser Cys Leu Lys Gly Cys Cys
                    1235                1240                1245

Ser Cys Gly Ser Cys Cys Lys Phe Asp Glu Asp Asp Ser Glu Pro Val
                    1250                1255                1260

Leu Lys Gly Val Lys Leu His Tyr Thr Leu Glu Ser Gly Gly Gly Ser
1265                1270                1275                1280

Ala Trp Ser His Pro Gln Phe Glu Lys Gly Gly Gly Ser Gly Gly Gly
                    1285                1290                1295

Ser Gly Gly Ser Ser Ala Trp Ser His Pro Gln Phe Glu Lys
                    1300                1305                1310

<210> SEQ ID NO 10
<211> LENGTH: 1273
<212> TYPE: PRT
<213> ORGANISM: Artificial Sequence
<220> FEATURE:
<223> OTHER INFORMATION: A synthetic sequence
<221> NAME/KEY: VARIANT
<222> LOCATION: (1)...(1273)
<223> OTHER INFORMATION: Xaa = Any Amino Acid

<400> SEQUENCE: 10

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Xaa Glu
                85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
```

```
            210                 215                 220
Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Tyr Val Gly Tyr Leu Gln Pro
                260                 265                 270

Arg Thr Phe Leu Leu Lys Tyr Asn Glu Asn Gly Thr Ile Thr Asp Ala
                275                 280                 285

Val Asp Cys Ala Leu Asp Pro Leu Ser Glu Thr Lys Cys Thr Leu Lys
            290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
                370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
                450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640
```

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn Leu
            1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
            1045                1050                1055

```
Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
        1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270

<210> SEQ ID NO 11
<211> LENGTH: 1273
<212> TYPE: PRT
<213> ORGANISM: Artificial Sequence
<220> FEATURE:
<223> OTHER INFORMATION: A synthetic sequence

<400> SEQUENCE: 11

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140
```

-continued

| | | | | | | | | | | | | |
|---|---|---|---|---|---|---|---|---|---|---|---|---|
|Tyr|His|Lys|Asn|Asn|Lys|Ser|Trp|Met|Glu|Ser|Glu|Phe|Arg|Val|Tyr|
|145| | | | |150| | | |155| | | |  |   |160|

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
        530                 535                 540

Gly Leu Ile Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val

```
              565                 570                 575
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990
```

```
Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn Leu
        1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
            1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
            1075                1080                1085

Phe Pro Arg Glu Gly Val Phe Val Ser Asn Gly Thr His Trp Phe Val
            1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
            1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
            1155                1160                1165

Ile Ser Gly Ile Asn Ala Ser Val Val Asn Ile Gln Lys Glu Ile Asp
            1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
            1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
            1235                1240                1245

Ser Cys Gly Ser Cys Cys Lys Phe Asp Glu Asp Ser Glu Pro Val
            1250                1255                1260

Leu Lys Gly Val Lys Leu His Tyr Thr
1265                1270

<210> SEQ ID NO 12
<211> LENGTH: 17
<212> TYPE: PRT
<213> ORGANISM: Homo sapiens

<400> SEQUENCE: 12

Cys Lys Lys Thr Thr Met Lys Ile Ile Pro Phe Asn Arg Leu Thr Ile
1               5                   10                  15

Gly

<210> SEQ ID NO 13
<211> LENGTH: 11
<212> TYPE: PRT
<213> ORGANISM: Homo sapiens

<400> SEQUENCE: 13

Tyr Leu Leu Lys Asp Leu Trp Gln Lys Arg Gln
1               5                   10
```

<210> SEQ ID NO 14
<211> LENGTH: 19
<212> TYPE: PRT
<213> ORGANISM: Homo sapiens

<400> SEQUENCE: 14

Gln Ser Gly Leu Tyr Phe Ile Lys Pro Leu Lys Ala Asn Gln Gln Phe
1               5                   10                  15

Leu Val Tyr

<210> SEQ ID NO 15
<211> LENGTH: 32
<212> TYPE: PRT
<213> ORGANISM: Homo sapiens

<400> SEQUENCE: 15

Asp Asn Gly Ile Ile Trp Ala Thr Trp Lys Thr Arg Trp Tyr Ser Met
1               5                   10                  15

Lys Lys Thr Thr Met Lys Ile Ile Pro Phe Asn Arg Leu Thr Ile Gly
            20                  25                  30

<210> SEQ ID NO 16
<211> LENGTH: 437
<212> TYPE: PRT
<213> ORGANISM: Homo sapiens

<400> SEQUENCE: 16

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
        35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
    130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
    210                 215                 220

Asp Gly Ser Val Asp Phe Lys Lys Asn Trp Ile Gln Tyr Lys Glu Gly
225                 230                 235                 240

```
Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
    290                 295                 300

Ala Tyr Phe Ala Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
    370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln Gln His His Leu Gly Gly Ala Lys
            420                 425                 430

Gln Ala Gly Asp Val
        435

<210> SEQ ID NO 17
<211> LENGTH: 443
<212> TYPE: PRT
<213> ORGANISM: Mus musculus

<400> SEQUENCE: 17

Met Ser Trp Ser Leu Gln Pro Pro Ser Phe Leu Leu Cys Cys Leu Leu
1               5                   10                  15

Leu Leu Phe Ser Pro Thr Gly Leu Ala Tyr Val Ala Thr Arg Asp Asn
                20                  25                  30

Cys Cys Ile Leu Asp Glu Arg Phe Gly Ser Phe Cys Pro Thr Thr Cys
            35                  40                  45

Gly Ile Ala Asp Phe Leu Ser Ser Tyr Gln Thr Asp Val Asp Asn Asp
    50                  55                  60

Leu Arg Thr Leu Glu Asp Ile Leu Phe Arg Ala Glu Asn Arg Thr Thr
65                  70                  75                  80

Glu Ala Lys Glu Leu Ile Lys Ala Ile Gln Val Tyr Tyr Asn Pro Asp
                85                  90                  95

Gln Pro Pro Lys Pro Gly Met Ile Asp Ser Ala Thr Gln Lys Ser Lys
            100                 105                 110

Lys Met Val Glu Glu Ile Val Lys Tyr Glu Ala Leu Leu Leu Thr His
        115                 120                 125

Glu Thr Ser Ile Arg Tyr Leu Gln Glu Ile Tyr Asn Ser Asn Asn Gln
    130                 135                 140

Lys Ile Thr Asn Leu Lys Gln Lys Val Ala Gln Leu Glu Ala Gln Cys
145                 150                 155                 160

Gln Glu Pro Cys Lys Asp Ser Val Gln Ile His Asp Thr Thr Gly Lys
```

165                 170                 175
Asp Cys Gln Glu Ile Ala Asn Lys Gly Ala Lys Glu Ser Gly Leu Tyr
                180                 185                 190

Phe Ile Arg Pro Leu Lys Ala Lys Gln Gln Phe Leu Val Tyr Cys Glu
            195                 200                 205

Ile Asp Gly Ser Gly Asn Gly Trp Thr Val Leu Gln Lys Arg Ile Asp
        210                 215                 220

Gly Ser Leu Asp Phe Lys Lys Asn Trp Ile Gln Tyr Lys Glu Gly Phe
225                 230                 235                 240

Gly His Leu Ser Pro Thr Gly Thr Thr Glu Phe Trp Leu Gly Asn Glu
                245                 250                 255

Lys Ile His Leu Ile Ser Met Gln Ser Thr Ile Pro Tyr Ala Leu Arg
            260                 265                 270

Ile Gln Leu Lys Asp Trp Asn Gly Arg Thr Ser Thr Ala Asp Tyr Ala
        275                 280                 285

Met Phe Arg Val Gly Pro Glu Ser Asp Lys Tyr Arg Leu Thr Tyr Ala
    290                 295                 300

Tyr Phe Ile Gly Gly Asp Ala Gly Asp Ala Phe Asp Gly Tyr Asp Phe
305                 310                 315                 320

Gly Asp Asp Pro Ser Asp Lys Phe Phe Thr Ser His Asn Gly Met Gln
                325                 330                 335

Phe Ser Thr Trp Asp Asn Asp Asn Asp Lys Phe Glu Gly Asn Cys Ala
            340                 345                 350

Glu Gln Asp Gly Ser Gly Trp Trp Met Asn Lys Cys His Ala Gly His
        355                 360                 365

Leu Asn Gly Val Tyr His Gln Gly Gly Thr Tyr Ser Lys Ser Ser Thr
        370                 375                 380

Thr Asn Gly Phe Asp Asp Gly Ile Ile Trp Ala Thr Trp Lys Ser Arg
385                 390                 395                 400

Trp Tyr Ser Met Lys Glu Thr Thr Met Lys Ile Ile Pro Phe Asn Arg
                405                 410                 415

Leu Ser Ile Gly Glu Gly Gln Gln His His Met Gly Gly Ser Lys Gln
            420                 425                 430

Val Ser Val Asp His Glu Val Glu Ile Glu Tyr
        435                 440

<210> SEQ ID NO 18
<211> LENGTH: 1152
<212> TYPE: PRT
<213> ORGANISM: Homo sapiens

<400> SEQUENCE: 18

Met Ala Leu Arg Val Leu Leu Thr Ala Leu Thr Leu Cys His Gly
1               5                   10                  15

Phe Asn Leu Asp Thr Glu Asn Ala Met Thr Phe Gln Glu Asn Ala Arg
                20                  25                  30

Gly Phe Gly Gln Ser Val Val Gln Leu Gln Gly Ser Arg Val Val Val
            35                  40                  45

Gly Ala Pro Gln Glu Ile Val Ala Ala Asn Gln Arg Gly Ser Leu Tyr
        50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

```
Thr Ser Pro Pro Gln Leu Leu Ala Cys Gly Pro Thr Val His Gln Thr
            100                 105                 110
Cys Ser Glu Asn Thr Tyr Val Lys Gly Leu Cys Phe Leu Phe Gly Ser
        115                 120                 125
Asn Leu Arg Gln Gln Pro Gln Lys Phe Pro Glu Ala Leu Arg Gly Cys
    130                 135                 140
Pro Gln Glu Asp Ser Asp Ile Ala Phe Leu Ile Asp Gly Ser Gly Ser
145                 150                 155                 160
Ile Ile Pro His Asp Phe Arg Arg Met Lys Glu Phe Val Ser Thr Val
                165                 170                 175
Met Glu Gln Leu Lys Lys Ser Lys Thr Leu Phe Ser Leu Met Gln Tyr
            180                 185                 190
Ser Glu Glu Phe Arg Ile His Phe Thr Phe Lys Glu Phe Gln Asn Asn
        195                 200                 205
Pro Asn Pro Arg Ser Leu Val Lys Pro Ile Thr Gln Leu Leu Gly Arg
    210                 215                 220
Thr His Thr Ala Thr Gly Ile Arg Lys Val Val Arg Glu Leu Phe Asn
225                 230                 235                 240
Ile Thr Asn Gly Ala Arg Lys Asn Ala Phe Lys Ile Leu Val Val Ile
                245                 250                 255
Thr Asp Gly Glu Lys Phe Gly Asp Pro Leu Gly Tyr Glu Asp Val Ile
            260                 265                 270
Pro Glu Ala Asp Arg Glu Gly Val Ile Arg Tyr Val Ile Gly Val Gly
        275                 280                 285
Asp Ala Phe Arg Ser Glu Lys Ser Arg Gln Glu Leu Asn Thr Ile Ala
    290                 295                 300
Ser Lys Pro Pro Arg Asp His Val Phe Gln Val Asn Asn Phe Glu Ala
305                 310                 315                 320
Leu Lys Thr Ile Gln Asn Gln Leu Arg Glu Lys Ile Phe Ala Ile Glu
                325                 330                 335
Gly Thr Gln Thr Gly Ser Ser Ser Phe Glu His Glu Met Ser Gln
            340                 345                 350
Glu Gly Phe Ser Ala Ala Ile Thr Ser Asn Gly Pro Leu Leu Ser Thr
        355                 360                 365
Val Gly Ser Tyr Asp Trp Ala Gly Gly Val Phe Leu Tyr Thr Ser Lys
    370                 375                 380
Glu Lys Ser Thr Phe Ile Asn Met Thr Arg Val Asp Ser Asp Met Asn
385                 390                 395                 400
Asp Ala Tyr Leu Gly Tyr Ala Ala Ala Ile Ile Leu Arg Asn Arg Val
                405                 410                 415
Gln Ser Leu Val Leu Gly Ala Pro Arg Tyr Gln His Ile Gly Leu Val
            420                 425                 430
Ala Met Phe Arg Gln Asn Thr Gly Met Trp Glu Ser Asn Ala Asn Val
        435                 440                 445
Lys Gly Thr Gln Ile Gly Ala Tyr Phe Gly Ala Ser Leu Cys Ser Val
    450                 455                 460
Asp Val Asp Ser Asn Gly Ser Thr Asp Leu Val Leu Ile Gly Ala Pro
465                 470                 475                 480
His Tyr Tyr Glu Gln Thr Arg Gly Gly Gln Val Ser Val Cys Pro Leu
                485                 490                 495
Pro Arg Gly Arg Ala Arg Trp Gln Cys Asp Ala Val Leu Tyr Gly Glu
            500                 505                 510
Gln Gly Gln Pro Trp Gly Arg Phe Gly Ala Ala Leu Thr Val Leu Gly
```

```
                515                 520                 525
Asp Val Asn Gly Asp Lys Leu Thr Asp Val Ala Ile Gly Ala Pro Gly
                530                 535                 540
Glu Glu Asp Asn Arg Gly Ala Val Tyr Leu Phe His Gly Thr Ser Gly
545                 550                 555                 560
Ser Gly Ile Ser Pro Ser His Ser Gln Arg Ile Ala Gly Ser Lys Leu
                565                 570                 575
Ser Pro Arg Leu Gln Tyr Phe Gly Gln Ser Leu Ser Gly Gly Gln Asp
                580                 585                 590
Leu Thr Met Asp Gly Leu Val Asp Leu Thr Val Gly Ala Gln Gly His
                595                 600                 605
Val Leu Leu Leu Arg Ser Gln Pro Val Leu Arg Val Lys Ala Ile Met
                610                 615                 620
Glu Phe Asn Pro Arg Glu Val Ala Arg Asn Val Phe Glu Cys Asn Asp
625                 630                 635                 640
Gln Val Val Lys Gly Lys Glu Ala Gly Glu Val Arg Val Cys Leu His
                645                 650                 655
Val Gln Lys Ser Thr Arg Asp Arg Leu Arg Glu Gly Gln Ile Gln Ser
                660                 665                 670
Val Val Thr Tyr Asp Leu Ala Leu Asp Ser Gly Arg Pro His Ser Arg
                675                 680                 685
Ala Val Phe Asn Glu Thr Lys Asn Ser Thr Arg Arg Gln Thr Gln Val
                690                 695                 700
Leu Gly Leu Thr Gln Thr Cys Glu Thr Leu Lys Leu Gln Leu Pro Asn
705                 710                 715                 720
Cys Ile Glu Asp Pro Val Ser Pro Ile Val Leu Arg Leu Asn Phe Ser
                725                 730                 735
Leu Val Gly Thr Pro Leu Ser Ala Phe Gly Asn Leu Arg Pro Val Leu
                740                 745                 750
Ala Glu Asp Ala Gln Arg Leu Phe Thr Ala Leu Phe Pro Phe Glu Lys
                755                 760                 765
Asn Cys Gly Asn Asp Asn Ile Cys Gln Asp Asp Leu Ser Ile Thr Phe
770                 775                 780
Ser Phe Met Ser Leu Asp Cys Leu Val Val Gly Gly Pro Arg Glu Phe
785                 790                 795                 800
Asn Val Thr Val Thr Val Arg Asn Asp Gly Glu Asp Ser Tyr Arg Thr
                805                 810                 815
Gln Val Thr Phe Phe Phe Pro Leu Asp Leu Ser Tyr Arg Lys Val Ser
                820                 825                 830
Thr Leu Gln Asn Gln Arg Ser Gln Arg Ser Trp Arg Leu Ala Cys Glu
                835                 840                 845
Ser Ala Ser Ser Thr Glu Val Ser Gly Ala Leu Lys Ser Thr Ser Cys
                850                 855                 860
Ser Ile Asn His Pro Ile Phe Pro Glu Asn Ser Glu Val Thr Phe Asn
865                 870                 875                 880
Ile Thr Phe Asp Val Asp Ser Lys Ala Ser Leu Gly Asn Lys Leu Leu
                885                 890                 895
Leu Lys Ala Asn Val Thr Ser Glu Asn Asn Met Pro Arg Thr Asn Lys
                900                 905                 910
Thr Glu Phe Gln Leu Glu Leu Pro Val Lys Tyr Ala Val Tyr Met Val
                915                 920                 925
Val Thr Ser His Gly Val Ser Thr Lys Tyr Leu Asn Phe Thr Ala Ser
                930                 935                 940
```

```
Glu Asn Thr Ser Arg Val Met Gln His Gln Tyr Gln Val Ser Asn Leu
945                 950                 955                 960

Gly Gln Arg Ser Leu Pro Ile Ser Leu Val Phe Leu Val Pro Val Arg
            965                 970                 975

Leu Asn Gln Thr Val Ile Trp Asp Arg Pro Gln Val Thr Phe Ser Glu
        980                 985                 990

Asn Leu Ser Ser Thr Cys His Thr Lys Glu Arg Leu Pro Ser His Ser
    995                 1000                1005

Asp Phe Leu Ala Glu Leu Arg Lys Ala Pro Val Val Asn Cys Ser Ile
1010                1015                1020

Ala Val Cys Gln Arg Ile Gln Cys Asp Ile Pro Phe Phe Gly Ile Gln
1025                1030                1035                1040

Glu Glu Phe Asn Ala Thr Leu Lys Gly Asn Leu Ser Phe Asp Trp Tyr
                1045                1050                1055

Ile Lys Thr Ser His Asn His Leu Leu Ile Val Ser Thr Ala Glu Ile
                1060                1065                1070

Leu Phe Asn Asp Ser Val Phe Thr Leu Leu Pro Gly Gln Gly Ala Phe
            1075                1080                1085

Val Arg Ser Gln Thr Glu Thr Lys Val Glu Pro Phe Glu Val Pro Asn
        1090                1095                1100

Pro Leu Pro Leu Ile Val Gly Ser Ser Val Gly Gly Leu Leu Leu Leu
1105                1110                1115                1120

Ala Leu Ile Thr Ala Ala Leu Tyr Lys Leu Gly Phe Phe Lys Arg Gln
                1125                1130                1135

Tyr Lys Asp Met Met Ser Glu Gly Gly Pro Pro Gly Ala Glu Pro Gln
            1140                1145                1150

<210> SEQ ID NO 19
<211> LENGTH: 158
<212> TYPE: PRT
<213> ORGANISM: Mus musculus

<400> SEQUENCE: 19

Thr Phe Asp Ser Pro Tyr Gln Val Arg Arg Met Arg Phe Ser Ala Gln
1               5                   10                  15

Leu Leu Gly Leu Leu Val Leu Trp Ile Pro Gly Ser Thr Ala Asp Ile
            20                  25                  30

Val Met Thr Gln Ala Ala Phe Ser Asn Pro Ile Thr Leu Gly Thr Ser
        35                  40                  45

Ala Ser Met Ser Cys Arg Ser Ser Lys Ser Leu Leu His Ser Ser Gly
    50                  55                  60

Ile Thr Tyr Leu Ser Trp Tyr Leu Gln Lys Pro Gly Gln Ser Pro Gln
65                  70                  75                  80

Leu Leu Ile Tyr Gln Met Ser Asn Leu Ala Ser Gly Val Pro Asp Arg
                85                  90                  95

Phe Ser Ser Ser Gly Ser Gly Thr Asp Phe Thr Leu Arg Ile Ser Arg
            100                 105                 110

Val Glu Ala Glu Asp Val Gly Val Tyr Tyr Cys Ala Gln Asn Leu Glu
        115                 120                 125

Leu Pro Leu Thr Phe Gly Ala Gly Thr Lys Leu Glu Leu Lys Arg Ala
    130                 135                 140

Asp Ala Ala Pro Thr Val Ser Ala Cys Thr Lys Gly Glu Phe
145                 150                 155
```

```
<210> SEQ ID NO 20
<211> LENGTH: 16
<212> TYPE: PRT
<213> ORGANISM: Mus musculus

<400> SEQUENCE: 20

Arg Ser Ser Lys Ser Leu Leu His Ser Ser Gly Ile Thr Tyr Leu Ser
1               5                   10                  15

<210> SEQ ID NO 21
<211> LENGTH: 7
<212> TYPE: PRT
<213> ORGANISM: Mus musculus

<400> SEQUENCE: 21

Gln Met Ser Asn Leu Ala Ser
1               5

<210> SEQ ID NO 22
<211> LENGTH: 9
<212> TYPE: PRT
<213> ORGANISM: Mus musculus

<400> SEQUENCE: 22

Ala Gln Asn Leu Glu Leu Pro Leu Thr
1               5

<210> SEQ ID NO 23
<211> LENGTH: 166
<212> TYPE: PRT
<213> ORGANISM: Mus musculus

<400> SEQUENCE: 23

Asn Thr Ala Phe Ala Gly Phe Gly Arg Asn Met Arg Ser Leu Phe Ser
1               5                   10                  15

Leu Gln Leu Leu Ser Thr Gln Asp Leu Ala Met Gly Trp Ser Cys Ile
                20                  25                  30

Ile Val Leu Leu Val Ser Thr Ala Thr Gly Val His Ser Gln Val Gln
            35                  40                  45

Leu Gln Gln Pro Gly Ala Glu Leu Val Arg Pro Gly Thr Ser Val Lys
        50                  55                  60

Leu Ser Cys Lys Ala Ser Gly Tyr Thr Phe Thr Ser Tyr Trp Ile His
65                  70                  75                  80

Trp Val Lys Gln Arg Pro Gly Gln Gly Leu Glu Trp Ile Gly Leu Ile
                85                  90                  95

Asp Pro Ser Asp Ser Tyr Thr Asn Tyr Asn Gln Lys Phe Arg Gly Lys
            100                 105                 110

Ala Thr Leu Thr Val Asp Thr Ser Ser Thr Ala Tyr Met Gln Leu
        115                 120                 125

Ser Ser Leu Thr Ser Glu Asp Ser Ala Val Tyr Tyr Cys Ala Ser Ser
        130                 135                 140

Asp Pro Thr Gly Cys Trp Gly Gln Gly Thr Thr Leu Thr Val Ser Pro
145                 150                 155                 160

Ala Ser Thr Thr Pro Pro
                165

<210> SEQ ID NO 24
<211> LENGTH: 10
<212> TYPE: PRT
<213> ORGANISM: Mus musculus
```

<400> SEQUENCE: 24

Gly Tyr Thr Phe Thr Ser Tyr Trp Ile His
1               5                   10

<210> SEQ ID NO 25
<211> LENGTH: 16
<212> TYPE: PRT
<213> ORGANISM: Mus musculus

<400> SEQUENCE: 25

Leu Ile Asp Pro Ser Asp Ser Tyr Thr Asn Tyr Asn Gln Lys Phe Arg
1               5                   10                  15

<210> SEQ ID NO 26
<211> LENGTH: 6
<212> TYPE: PRT
<213> ORGANISM: Mus musculus

<400> SEQUENCE: 26

Ser Asp Pro Thr Gly Cys
1               5

<210> SEQ ID NO 27
<211> LENGTH: 474
<212> TYPE: DNA
<213> ORGANISM: Mus musculus

<400> SEQUENCE: 27

```
acttttgact caccatatca agttcgcaga atgaggttct ctgctcagct tctggggctg    60
cttgtgctct ggatccctgg atccactgca gatattgtga tgacgcaggc tgcattctcc   120
aatccaatca ctcttggaac atcagcttcc atgtcctgca ggtctagtaa gagtctccta   180
catagtagtg gcatcactta tttgtcttgg tatctgcaga agccaggcca gtctcctcag   240
ctcctgattt atcagatgtc caaccttgcc tcaggagtcc cagacaggtt cagtagcagt   300
gggtcaggaa ctgatttcac actgagaatt agccgagtgg aggctgagga tgtgggtgtt   360
tattactgtg ctcaaaatct agaacttccg ctcacgttcg gtgctgggac caagctggag   420
ctgaaacggg ctgatgctgc accaactgta tccgcatgca ccaagggcga attc         474
```

<210> SEQ ID NO 28
<211> LENGTH: 498
<212> TYPE: DNA
<213> ORGANISM: Mus musculus

<400> SEQUENCE: 28

```
aacactgcgt tgctggcttt tggaagaaac atgagatcac tgttctctct acagttactg    60
agcacacagg acctcgccat gggatggagc tgtatcattg tcctcttggt atcaacagct   120
acaggtgtcc actcccaggt ccaactgcag cagcctgggg ctgagctggt gaggcctggg   180
acttcagtga agttgtcctg caaggcttct ggctacacct tcaccagcta ctggatacac   240
tgggtaaagc agaggcctgg acaaggcctt gagtggatcg gactgattga tccttctgat   300
agttatacta actacaatca aaagttcagg ggcaaggcca cattgactgt agacacatcc   360
tccagcacag cctacatgca gctcagcagc ctgacatctg aggactctgc ggtctattac   420
tgtgcaagct ccgatcctac aggctgctgg ggccaaggca ccactctcac agtctcccca   480
gctagcacaa caccccca                                                  498
```

<210> SEQ ID NO 29

```
<211> LENGTH: 48
<212> TYPE: DNA
<213> ORGANISM: Mus musculus

<400> SEQUENCE: 29
aggtctagta agagtctcct acatagtagt ggcatcactt atttgtct            48

<210> SEQ ID NO 30
<211> LENGTH: 20
<212> TYPE: DNA
<213> ORGANISM: Mus musculus

<400> SEQUENCE: 30
cagatgtcca accttgcctc                                           20

<210> SEQ ID NO 31
<211> LENGTH: 27
<212> TYPE: DNA
<213> ORGANISM: Mus musculus

<400> SEQUENCE: 31
gctcaaaatc tagaacttcc gctcacg                                   27

<210> SEQ ID NO 32
<211> LENGTH: 30
<212> TYPE: DNA
<213> ORGANISM: Mus musculus

<400> SEQUENCE: 32
ggctacacct tcaccagcta ctggatacac                                30

<210> SEQ ID NO 33
<211> LENGTH: 51
<212> TYPE: DNA
<213> ORGANISM: Mus musculus

<400> SEQUENCE: 33
ctgattgatc cttctgatag ttatactaac tacaatcaaa agttcagggg c         51

<210> SEQ ID NO 34
<211> LENGTH: 18
<212> TYPE: DNA
<213> ORGANISM: Mus musculus

<400> SEQUENCE: 34
tccgatccta caggctgc                                             18
```